US008821899B2

(12) United States Patent  (10) Patent No.: US 8,821,899 B2
Peppas et al.  (45) Date of Patent: *Sep. 2, 2014

(54) METHOD AND PROCESS FOR THE PRODUCTION OF MULTI-COATED RECOGNITIVE AND RELEASING SYSTEMS

(75) Inventors: Nicholas A. Peppas, Austin, TX (US); Barbara Ekerdt, Austin, TX (US); Marta Gomez-Burgaz, Madrid (ES)

(73) Assignee: Board of Regents, The University of Texas System, Austin, TX (US)

( * ) Notice: Subject to any disclaimer, the term of this patent is extended or adjusted under 35 U.S.C. 154(b) by 449 days.

This patent is subject to a terminal disclaimer.

(21) Appl. No.: 12/328,469

(22) Filed: Dec. 4, 2008

(65) Prior Publication Data

US 2009/0232857 A1 Sep. 17, 2009

Related U.S. Application Data

(63) Continuation-in-part of application No. 12/047,309, filed on Mar. 12, 2008.

(60) Provisional application No. 60/894,451, filed on Mar. 12, 2007.

(51) Int. Cl.
A61K 9/00 (2006.01)
A61K 9/14 (2006.01)
A61K 8/73 (2006.01)
A61K 9/70 (2006.01)
A61Q 13/00 (2006.01)
B82Y 5/00 (2011.01)
A61K 47/34 (2006.01)
A61K 8/02 (2006.01)
A61K 9/50 (2006.01)
A61Q 17/00 (2006.01)
A61K 31/137 (2006.01)
A61K 38/28 (2006.01)
A61K 47/48 (2006.01)

(52) U.S. Cl.
CPC .............. A61K 31/137 (2013.01); A61K 8/731 (2013.01); A61K 9/7007 (2013.01); A61Q 13/00 (2013.01); B82Y 5/00 (2013.01); A61K 47/34 (2013.01); A61K 8/0279 (2013.01); A61K 8/0241 (2013.01); A61K 2800/413 (2013.01); A61K 9/0004 (2013.01); A61K 9/7015 (2013.01); A61K 9/5031 (2013.01); A61Q 17/005 (2013.01); A61K 38/28 (2013.01); A61K 9/5073 (2013.01); A61K 47/48784 (2013.01); A61K 9/0014 (2013.01); A61K 8/025 (2013.01)
USPC ........................... 424/400; 424/486; 424/487

(58) Field of Classification Search
USPC ................. 424/400, 464, 486, 487; 526/72
See application file for complete search history.

(56) References Cited

U.S. PATENT DOCUMENTS

| 3,538,214 | A | 11/1970 | Polli et al. |
| 4,228,149 | A | 10/1980 | Brewer et al. |
| 6,303,148 | B1 | 10/2001 | Hennink et al. |
| 6,897,271 | B1 | 5/2005 | Domschke et al. |
| 7,176,247 | B1 | 2/2007 | Walker, Jr. |
| 7,459,316 | B2 | 12/2008 | Faid et al. |
| 8,062,769 | B2 | 11/2011 | Kai et al. |
| 2002/0071877 | A1 | 6/2002 | Mueller |
| 2003/0059471 | A1 | 3/2003 | Compton et al. |
| 2004/0091541 | A1 | 5/2004 | Unger |
| 2005/0008686 | A1 | 1/2005 | Mannino et al. |
| 2005/0249721 | A1 | 11/2005 | Houston et al. |
| 2005/0276781 | A1* | 12/2005 | Ross et al. ................ 424/78.08 |
| 2007/0027213 | A1 | 2/2007 | Oberegger et al. |
| 2007/0134721 | A1 | 6/2007 | Laitenberger et al. |
| 2008/0171067 | A1 | 7/2008 | Serengulam et al. |
| 2008/0226684 | A1 | 9/2008 | Peppas |
| 2009/0081265 | A1 | 3/2009 | Peppas |
| 2009/0232858 | A1 | 9/2009 | Peppas |

FOREIGN PATENT DOCUMENTS

| EP | 1664168 B1 | 3/2008 |
| WO | 02/071994 A1 | 9/2002 |
| WO | 2005020849 A2 | 3/2005 |
| WO | WO/2006/116734 | * 11/2006 |
| WO | 2008056746 A2 | 5/2008 |
| WO | 2008112826 A1 | 9/2008 |

OTHER PUBLICATIONS

Peppas et al., B.T Gattefosse. 2003, vol. 96, pp. 25-38.*
Alvarez-Lorenzo, C., et al., "Polymer gels that memorize elements of molecular conformation." Macromolecules (2000), 33:8693-8697.
Alvarez-Lorenzo, C., et al., "Reversible adsorption of calcium ions by imprinted temperature sensitive gels." J Chem Phys (2001), 114:2812-2816.
Alvarez-Lorenzo, C., et al., "Simultaneous multiple-point adsorption of aluminum ions and charged molecules a polyampholyte thermosensitive gel: Controlling frustrations in a heteropolymer gel." Langmuir (2001), 17:3616-3622.
Alvarez-Lorenzo, C. H., et al., "Soft contact lenses capable of sustained delivery of timolol." J Pharm Sci (2002), 91:2182.
Ansell, R. J., et al., "Molecularly imprinted polymers for bioanalysis: Chromatography, binding assays and biomimetic sensors." Curr Opin Biotechnol (1996), 7:89-94.
Bashir, R., et al., "Micromechanical cantilever as an ultrasensitive pH microsensor." Appl Phys Lett (2002), 81:3091-3093.
Bures, P., et al., "Surface modifications and molecular imprinting of polymers in medical and pharmaceutical applications." J Controlled Release (2001), 72:25-33.

(Continued)

Primary Examiner — Renee Claytor
Assistant Examiner — Shobha Kantamneni
(74) Attorney, Agent, or Firm — Chainey P. Singleton; Edwin S. Flores; Chalker Flores, LLP

(57) ABSTRACT

The present invention includes compositions, methods, systems for the controlled delivery of an active agent within a polymeric network upon the binding of a molecule that decreases the structural integrity of the polymeric network at one or more micro- or nanovacuoles.

8 Claims, 7 Drawing Sheets

(56) References Cited

OTHER PUBLICATIONS

Byrne, M., et al., "Molecular imprinting within hydrogels." Advanced Drug Delivery Reviews (2002), 54:149-161.
Byrne, M., et al., "Networks for recognition of biomolecules: Molecular imprinting and micropatterning poly(ethylene glycol)-containing films." Polym Advan Technol (2002), 13:798-816.
Hilt, J.Z., et al., "Ultrasensitive Biomems Sensors Based on Microcantilevers Patterned with Environmentally Responsive Hydrogels." Biomedical Microdevices, (2003), 5(3):177-184."
Chen, B N., et al., "Molecular recognition: Design of 'keys'." Comb Chem High Throughput Screen (2002), 5:409-427.
Hilt, J Z., et al., "Ultrasensitive biomems sensors based on microcantilevers patterned with environmentally responsive hydrogels." Biomed Microdevices (2003), 5:177-184.
Hilt, J. Z., "Nanotechnology and biomimetic methods in therapeutics: molecular scale control with some help from nature." Adv Drug Deliv Rev (2004), 56:1533-1536.
Mosbach, K., "Molecular imprinting." Trends in Biochemical Sciences (1994), 19:9-14.
Mosbach, K. "Toward the next generation of molecular imprinting with emphasis on the formation, by direct molding, of compounds with biological activity (biomimetics)." Analytica Chimica Acta (2001), 435:3-8.
Oral, E., et al., "Responsive and recognitive hydrogels using star polymers." J Biomed Mater Res A (2004), 68A:439-447.
Peppas, N. A., "Intelligent biomaterials as pharmaceutical carriers in microfabricated and nanoscale devices." MRS Bulletin (2006), 31:888-893.
Ward, J., et al., "Micropatterning of biomedical polymer surfaces by novel UV polymerization techniques." J Biomed Mater Res (2001), 56:351-360.
Wulff, G., et al., "Enzyme-Analogue Built Polymers. 4. Synthesis of Polymers Containing Chiral Cavities and Their Use for Resolution of Racemates." Makromolekulare Chemie-Macromolecular Chemistry and Physics (1977), 178:2799-2816.
Wulff, G., et al., "Enzyme-analogue built polymers. 5. Specificity distribution of chiral cavities prepared in synthetic-polymers." Makromolekulare Chemie-Macromolecular Chemistry and Physics (1977), 178:2817-2825.
Wizeman, William J., et al., "Molecularly Imprinted Polymer Hydrogels Displaying Isomerically Resolved Glucose Binding," Biomaterials, (2001), 22:1485-1491.
Andersson, et al. "Imprinting of Amino Acid Derivatives in Macroporous Polymers" Tetrahedron Letters, 1984. 25(45): pp. 5211-5214.
Andersson, et al. "Study of the nature of recognition in molecularly imprinted polymers, II. [1] Influence of monomer-template ratio and sample load on retention and selectivity" J. Chromatogr. A, 1999. 848: p. 39-49.
Andersson, et al. "Mimics of the Binding Sites of Opiod Receptors Obtained by Molecular Imprinting of Enkephalin and Morphine" Proc. Natl. Acad. Sci. USA, 1995. 92: p. 4788-4792.
Appella, et al. "Peptide Foldamers: Robust Helix Formation in a New Family of Beta-Amino Acid Oligomers" J. Am. Chem. Soc., 1996. 118: p. 13071-13072.
Badiger, M.V. "Porogens in the preparation of microporous hydrogels based on poly(ethylene oxides)" Biomaterials (1993), 14:1059-1063.
Bartsch, et al. "Molecular and Ionic Recognition with Imprinted Polymers: A Brief Overview"—Book Abstract—8 pages.
Bergmann, et al. "Protein-Imprinted Polymeric Microparticles for Tissue Engineering Applications" 2003 Society for Biomaterials 29th Annual Meeting Transactions, Trans Soc. Biomat 2003:29:457.
Berman, et al. "The Protein Data Bank" Nucleic Acids Res., 2000. 28: p. 235-242.
Bolisay, et al. "Separation of baculoviruses using configurationally biomimetic imprinted polymer hydrogels" Mat. Res. Soc. Symp. Proc., 2004. 787: p. G3.1/1-G3.1/5.

Breinl, et al. "Chemical Investigation of the Precipitate from Hemoglobin and Anti-hemoglobin Serum and Remarks on the Nature of Antibodies" Z. Physiol. Chem., 1930. 192: p. 45.
Burnet, F.M. "A Modification of Jerne's Theory of Antibody Production Using the Concept of Clonal Selection" Aust. J. Sci., 1957. 20: p. 67.
Burt, S. "Essential Oils: their antibacterial properties and potential applications in food—a review" International Journal of Food Microbiology 94 (2004) pp. 223-253.
Burton, D.R. "Monoclonal Antibodies from Combinatorial Libraries" Accounts Chem. Res., 1993. 26: p. 405-411.
Byrne, et al. "Biomimetic Networks for Selective Recognition of Biomolecules" 2002: Materials Research Society.
Byrne, M.E. Biomimetic Materials for Recognition of Biomolecules: Recognitive Networks for Drug Delivery and Bionanotechnology, in Chemical Engineering. Dec. 2003, Thesis, Purdue University: West Lafayette, IN.
Byrne, et al. "Micropatterning Biomimetic Materials for Bioadhesion and Drug Delivery" Purdue University: West Lafayette, IN. pp. 443-470.
Canal, et al. "Correlation between mesh size and eqilibrium degree of swelling of polymeric networks" J. Biomed. Mater. Res. (1989) 23, 1183.
Cederfur, et al. "Synthesis and Screening of a Configurationally biomimetic imprinted Polymer Library Targeted for Penicillin" G. J. Comb. Chem., 2003. 5: p. 67-72.
Chang, et al. "Preparation of alginate complex capsules containing eucalyptus essential oil and its controlled release" Colloids and Surfaces B: Biointerfaces 32 (2003) pp. 257-262.
Cormack, et al. "Molecular imprinting: recent developments and the road ahead" Reactive and Functional Polymers, 1999. 41: p. 115-124.
Dado, et al. "Intramolecular Hydrogen Bonding in Derivatives of Beta-Alanine and Gamma-Amino Butyric Acid: Model Studies for the Folding of Unnatural Polypeptide Backbones." J. Am. Chem. Soc., 1994. 116: p. 1054-1062.
Davies, et al. "Antibody Structure" Accounts Chem. Res., 1993. 26: p. 421-427.
Duclairoir, et al., "Evaluation of gliadins nanoparticles as drug delivery systems: a study of three different drugs" International Journal of Pharmaceutics, 253 (2003) p. 133-144.
Egholm, et al. "Peptide nucleic acids (PNA). Oligonucleotide analogues with an achiral peptide backbone" J. Am. Chem. Soc., 1992. 114: p. 1895-1897.
Franzios, et al. "Insecticidal and genotoxic activities of mint essential oils" Journal of Agricultural and Food Chemistry, 45 (1997) pp. 2690-2694.
Gellman, S.H. "Foldamers: A Manifesto" Accounts Chem. Res., 1998. 31: p. 173-180.
Harris, et al. "Refined Structure of an Intact IgG2a Monoclonal Antibody" Biochem., 1997. 36: p. 1581-1597.
Hartmans, et al. "Report of the Meeting of the Section Physiology of the EAPR, Jun. 20-24, 1994" Potato Research, 37 (1994) pp. 435-463.
Hartmans, et al. "Use of talent (carvone) as a sprout growth regulator of seed potatoes and the effect on stm and tuber number" Potato Research, 41 (1998) pp. 190-191.
Haupt, et al. "Imprinted polymer-based enantioselective acoustic sensor using a quartz crystal microbalance" Anal. Commun., 1999. 36.
Herr, et al., J. Am. Chem. Soc. 89:4808-09 (1967).
Hilt, et al. "Configurational biomimesis in drug delivery: molecular imprinting of biologically significant molecules" Advanced Drug Delivery Reviews 56 (2004) 1599-1620.
Hilt, et al. "Novel Biomimetic Polymer Networks: Development and Application as Selective Recognition Elements for Biomolecules at the Micro-/Nanoscale" in AIChE Nanoscale Science and Engineering Topical Conference Proceedings. 2003. San Francisco, CA.
International Search Report for PCT/US2008/056746 dated Jun. 24, 2008.
Jerne, N.K. "The Generative Grammar of the Immune System, in Nobel Lectures" Physiology or Medicine 1981-1990, J. Lindsten, Editor. 1993, World Scientific Publishing Co.: Singapore. p. 211-225.

(56) References Cited

OTHER PUBLICATIONS

Jerne, N.K. "The Natural Selection Theory of Antibody Formation" Proc. Natl. Acad. Sci. USA, 1955. 41: p. 849.
Kabiri, et al. "Novel approach to highly porous superabsorbent hydrogels: synergistic effect of porogens on porosity and swelling rate" Polymer International (2003), 52:1158-1164.
Karmalkar, et al. "Configurationally biomimetic imprinted Hydrogels Exhibit Chymotrypsin-like Activity" Macromolecules, 1996. 29: p. 1366-1368.
Kempe, et al. "An approach towards surface imprinting using the enzyme ribonuclease" A. J. Mol. Recognition, 1995. 8(1-2): p. 35-39.
Kempe, et al. "Separation of amino acids, peptides and proteins on configurationally biomimetic imprinted stationary phases" J. Chromatogr. A, 1995. 691: p. 317-323.
Kirshenbaum, et al. "Designing polymers that mimic biomolecules" Current Opinion in Structural Biology, 1999. 9: p. 530-535.
Kirshenbaum, et al. "Sequence-specific polypeptoids: A diverse family of heteropolymers with stable secondary structure" Proc. Natl. Acad. Sci. USA, 1998. 95: p. 4303-4308.
Koehl, et al. "De Novo Protein Design. I. In Search of Stability and Specificity" J. Mol. Biol., 1999. 293: p. 1161-1181.
Koehl, et al. "De Novo Protein Design. II. Plasticity in Sequence Space" J. Mol. Biol., 1999. 293: p. 1183-1193.
Kohler, et al. "Continuous cultures of fused cells secreting antibody of predefined specificity" Nature, 1975. 256: p. 495-497.
Köhler, G.J.F. "Derivation and Diversification of Monoclonal Antibodies, in Nobel Lectures" Physiology or Medicine 1981-1990, J. Lindsten, Editor. 1993, World Scientific Publishing Co.: Singapore. p. 228-243.
Komiyama, et al. "Molecular Imprinting From Fundamentals to Applications" 2003, Weinheim, Germany: Wiley-VCH.
Kriz, et al. "Thin-Layer Chromatography Based on the Molecular Imprinting Technique" Anal. Chem., 1994. 66: p. 2636-2639.
Liang, et al. "Molecular imprinting polymer coated BAW bio-mimic sensor for direct determination of epinephrine" Anal. Chim. Acta, 2000. 415: p. 135-141.
Merrifield, R.B. "Solid Phase Peptide Synthesis. I. The Synthesis of a Tetrapeptide" J. Am. Chem. Soc., 1963. 85: p. 2149-2154.
Merrifield, R.B. "Solid Phase Peptide Synthesis. II. The Synthesis of Bradykinin" J. Am. Chem. Soc., 1964. 86: p. 304.
Merrifield, R.B. "Solid-Phase Peptide Synthesis, III. An Improved Synthesis of Bradykinin" Biochem., 1964. 3: p. 1385-1390.
Merrifield, R.B.. "Solid Phase Synthesis, in Nobel Lectures" Chemistry 1981-1990, T. Frängsmyr, Editor. 1992, World Scientific Publishing Co.: Singapore. p. 149-175.
Milstein, C. "From the Structure of Antibodies to the Diversification of the Immune Response, in Nobel Lectures" Physiology or Medicine 1981-1990, J. Lindsten, Editor. 1993, World Scientific Publishing Co.: Singapore. p. 248-270.
Mosbach, et al. "The Emerging Technique of Molecular Imprinting and its Future Impact on Biotechnology" Biotechnol., 1996. 14: p. 163-170.
Omidian, et al. "Advances in superporous hydrogels" J. Controlled Release (2005), 102:3-12.
Pande, et al. "Thermodynamic procedure to synthesize heteropolymers that can renature to recognize a given target molecule" Proc. Natl. Acad. Sci. USA, 1994.91: p. 12976-12979.
Pande, et al. "How to Create Polymers with Protein-Like Capabilities: A Theoretical Suggestion" Physica D, 1997. 107: p. 316-321.
Pande, et al. "Phase diagram of heteropolymers with an imprinted conformation" Macromolecules, 1995. 28: p. 2218-2227.
Pande, et al. "Folding Thermodynamics and kinetics of imprinted renaturable heteropolymers" J. Chem. Phys., 1994. 101(9): p. 8246-8257.
Parmpi, et al. "Biomimetic glucose recognition using configurationally biomimetic imprinted hydrogels" Biomaterials, 2004. 25: p. 1969-1973.
Pauling, L. "A Theory of the Structure and Process of Formation of Antibodies" J. Am. Chem. Soc., 1940. 62: p. 2643-2657.
Peppas, et al. "Advances in Biomaterial, Drug Delivery, and Bionanotechnology" AIChE J., 2003 49(12): p. 2990-3006.
Peppas, et al. "Controlled Release of fragrance from polymers I. Thermodynamic analysis" Journal of Controlled Release 40 (1996) 245-250.
Peppas, et al. "Controlled release of perfumes from polymers. II. Incorporation and release of essential oils from glassy polymers" Journal of Applied Polymer Science, vol. 66 (1997) pp. 509-513.
Rachkov, et al. "Towards Molecularly imprinted Polymers Selective to Peptides and Proteins" The Epitope Approach. Biochimica et Biophysica Acta, 2001. 1544: p. 255-266.
Ramstrom, et al. "Synthesis and catalysis by molecularly imprinted materials" Curr. Opin. Chem. Biol., 1999. 3: p. 759-764.
Ratner, B.D. "The Engineering of Biomaterials Exhibiting Recognition and Specificity" J. Mol. Recognition, 1996. 9: p. 617-625.
Robinson, et al. "Molecular imprinting of a transition state analogue leads to a polymer exhibiting esterolytic activity" J. Chem. Soc. Chem. Commun., 1989. 14: p. 969-970.
Sanchez, et al. "Migration models for polymer additives" Polym. News 6 (1980) 249-256.
Sanchez, I.C. "Equilibrium distribution of a minor constituent between a polymer and its environment, in Durability of Macromolecular Materials" R.K. Eby, ed. ACS Symp. Ser. vol. 95, American Chemical Society, Washington, DC, 1979, pp. 171-181.
Secouard, et al. "Release of limonene from polysaccharide matrices: viscosity and synergy effect" Food Chemistry 82 (2003) 227-234.
Sellergren, et al. "Enantioselective ester hydrolysis catalyzed by imprinted polymers" Tetrahedron-Asymmetry, 1994. 5: p. 1403-1406.
Shakhnovich, et al. "Engineering of stable and fast-folding sequences of model proteins" Proc. Natl. Acad. Sci. USA, 1993. 90: p. 7195-7199.
Shnek, et al. "Specific Protein Attachment to Artificial Membranes via Coordination to Lipid-Bound Copper(II)" Langmuir, 1994. 10: p. 2382-2388.
Talmage, D.W. "Allergy and Immunology" Ann. Rev. Med., 1957. 8: p. 239.
Tormo, et al. "Crystal Structure of a Human Rhinovirus Neutralizing Antibody Complexed with a Peptide Derived from Viral Capsid Protein VP2" EMBO J., 1994. 13: p. 2247-2256.
Vlatakis, et al. "Drug assay using antibody mimics made by molecular imprinting" Nature, 1993. 361: p. 645-647.
Venton, et al. "Influence of protein on polysiloxane polymer formation: evidence for induction of complementary protein-polymer interactions" Biochim. Biophys. Acta, 1995. 1250: p. 126-136.
Wulff, et al. "Enzyme-Analogue Built Polymers and Their Use for the Resolution of Racemates" Tetrahedron Letters, 1973. 44: p. 4329-4332.
Yu, et al. "Influence of mobile phase composition and cross-linking density on the enantiomeric recognition properties of configurationally biomimetic imprinted polymers" J. Chromatogr. A, 2000. 888: p. 63-72.
Yue, et al. "Inverse Protein Folding Problem: Designing Polymer Sequences" Proc. Natl. Acad. Sci. USA, 1992. 89: p. 4163-4167.

\* cited by examiner

METHOD AND PROCESS FOR THE PRODUCTION OF MULTI-COATED RECOGNITIVE AND RELEASING SYSTEMS

CROSS-REFERENCE TO RELATED APPLICATIONS

This application claims priority to U.S. Provisional Application Ser. No. 60/894,451, filed Mar. 12, 2007, and is a continuation-in-part of U.S. patent application Ser. No. 12/047,309, filed Mar. 12, 2008, the entire contents of which are incorporated herein by reference.

TECHNICAL FIELD OF THE INVENTION

The present invention relates in general to the field of the controlled release of agents, and more particularly, to novel compositions and methods for making controlled release configurational biomimetic imprinting networks.

STATEMENT OF FEDERALLY FUNDED RESEARCH

None.

BACKGROUND OF THE INVENTION

Without limiting the scope of the invention, its background is described in connection with the recognition and controlled release of active agents from polymers.

U.S. Pat. No. 7,459,316, issued to Faid, et al., is directed to a Molecularly-Imprinted Chemical Detection Device and Method. Briefly, a novel method of molecular imprinting is described that uses a modified soft lithography technique, a molecularly-imprinted chemical detection device comprising at least one molecularly-imprinted polymer capable of detecting at least one chemical target is produced. The device can be used in the field for in situ detection and quantification of chemical targets using standard surface analytical techniques.

U.S. Pat. No. 7,176,247, issued to Walker, teaches an interpenetrating polymer network. Briefly, a water insoluble interpenetrating polymer network is obtained by independently cross-linking a first polymer derived from a sulfonic acid or phosphonic acid group containing alkenyl monomer and a second polymer polymerized independently of the first polymer and interpenetrating the first polymer, where the second polymer is selectively permeable to water compared to methanol. Through adjustment of the degree of first polymer monomer acidification, polymer ratios and the extent of cross-linking in the at least two interpenetrating polymers, ion conductivity and solvent permeability are controlled. The relative degree and mechanism of cross-linking and interpenetrating the first polymer and second polymer are also adjustable parameters that impact on film properties.

U.S. Patent Application Ser. No. 20080171067, filed by Serengulam, et al., is directed to Polymeric Carriers of Therapeutic Agents and Recognition Moieties for Antibody-Based Targeting of Disease Sites. Briefly, the disclosure teaches methods and compositions for delivery of therapeutic agents to target cells, tissues or organisms. In preferred embodiments, the therapeutic agents are delivered in the form of therapeutic-loaded polymers that may comprise many copies of one or more therapeutic agents. The polymer may be conjugated to a peptide moiety that contains one or more haptens, such as HSG. The agent-polymer-peptide complex may be delivered to target cells by, for example, a pre-targeting technique utilizing bispecific or multispecific antibodies or fragments, having at least one binding arm that recognizes the hapten and at least a second binding arm that binds specifically to a disease or pathogen associated antigen, such as a tumor associated antigen. Methods for synthesizing and using such therapeutic-loaded polymers and their conjugates are provided.

SUMMARY OF THE INVENTION

The needs of the invention set forth above as well as further and other needs and advantages of the present invention are achieved by the embodiments of the invention described herein below. The present invention is based on the recognition that, to date, imprinted or recognitive polymers are found in two forms, solid and gel-like. Solid recognitive polymers are used in a variety of applications, namely, chromatography, filters and molecular separation. The other category of imprinted polymers are gelatinous polymers that are loaded with a payload during the polymerization phase and are dried until use. Upon exposing these gelatinous imprinted polymers to a solvent, e.g., water and/or water with the analyte or recognitive molecules, the gelatinous polymers swell. Unfortunately, for the delivery of most payloads swelling of the gelatinous polymer in the presence of solvent alone leads to leakage of the payload. What are needed are compositions, methods and systems for the delivery of payloads under recognitive control that do not leak and that are amenable to controlled release upon exposure to the analyte.

The present invention also includes a method of making a polymeric recognitive network that includes selecting one or more targets for recognition; forming micro- or nano-vacuoles in the polymeric recognitive network about the one or more targets; embedding within the polymeric recognitive network one or more active agents for release upon dissociation of the polymeric recognitive network; and removing the targets from the micro- or nano-vacuoles, wherein subsequent binding of the target to the micro- or nano-vacuoles causes disruption of the polymeric recognitive network and release of the one or more active agents.

Yet another embodiment of the present invention includes a kit for making a polymeric recognitive network that includes one or more targets for recognition by the polymeric recognitive network; monomers for forming a polymeric recognitive network comprising micro- or nano-vacuoles about the one or more targets; a polymeric catalyst for forming the polymeric recognitive network about the targets; and instructions for polymerizing the polymeric recognitive network and removing the targets from the micro- or nano-vacuoles and loading of the polymeric recognitive network with one or more active agents.

According to one embodiment, the present disclosure provides a system for forming multilayer mimetic structures that comprise a core and coating materials, including molecularly imprinted polymers, materials for use as a spacer, and materials for use as a binder. According to another embodiment, the present disclosure provides a system for forming multilayer mimetic structures wherein the core comprises spherical or non-spherical compositions, molecularly imprinted polymers, hydroxyl propyl cellulose (HPC) as a spacer and mannitol as a binder. According to another embodiment, the present disclosure provides a system for forming multilayer mimetic structures in which the molecularly imprinted polymer layer with controllable properties for bursting and drug release.

According to another embodiment, the present disclosure provides methods for controlling bursting and release of molecularly imprinted polymer layers by manipulation of various factors including, but not limited to, disintegration kinetics, tensile strength of the polymers via crosslinking and intrapolymer complexes, molecular weight, pressure differences by use of osmotic agents, and thickness of the layer.

The present invention includes a molecule-imprinted polymeric network that includes a polymer or gel comprising one or more micro- or nanovacuoles, or micro- or nanopores wherein the nanovacuoles or nanopores recognize a specific molecule while subsequent contact with the molecule creates internal stresses that rupture the polymeric network at the micro-or nanovacuoles or micro- or nanopores. Upon exposure of the polymeric network to the analyte, but not the solvent alone, the polymeric network can rupture due to, e.g., osmosis upon recognition and binding of the molecule leading to rupture due to swelling; change of the solubility of the polymeric network leading to polymer dissolution; local temperature changes leading to expansion of the polymeric network and combinations thereof. The composition may be loaded with one or more active agents to form an active agent-loaded, molecule-imprinted network. In one aspect of the invention, the polymer swells between 2-20, 4-18, 5-15, 8-12 and 10 percent of the dried polymer upon exposure to the solvent alone. In one aspect, the polymeric network swell between 5-15% of the dried polymeric network in the presence of the solvent alone.

Examples of active agents for use with the present invention include pharmaceutical and medical applications, food components, detergents, bleaches, fabric softeners, fragrances, cosmetic products, air fresheners, room deodorant devices, perfumed substrates, perfumed plastics and pet collars. Other actives include food and cosmetic applications that use hydrocolloids as imprinting carriers for polymers of high molecular weight, wherein the hydrocolloids are extracted from plants, seaweeds or animal collagen, produced by microbial synthesis, and comprise polysaccharides, proteins and combinations thereof. The molecule-imprinted network may be a carbohydrate polymer of glycosidic type mono-sugar repeative units, galactomannans, pectins, alginates, carrageenans and xanthan gum that are linear or branched, neutral or anionic and combinations thereof. Other examples include household products selected from laundry care; paper products; specialty cleaners (chlorinated cleaners, scouring pads, effervescent toilet bowl cleaner powders); air fresheners and combinations thereof. Further examples include personal care products selected from hair care (shampoos, hair mousses, styling agents); skin care (body lotions, vitamin e, aloe vera); bath products (moisture-triggered release products); body powders; toilet soap (milled or poured, ionic strength-triggered release) and combinations thereof. Also, cosmetics and treatment products selected from lipstick; eye-liner; foundation; base; blush; mascara; eye shadow; lip liner; facial powder; consealer; facial cream; make-up remover; mascara remover; make-up; skin treatments and may even include one or more fragrances or carriers therefore that include cologne; perfume; sampling; anti-perspirant; deodorant; anti-dandruff shampoos; athlete foot products and combinations thereof. Other actives include a surfactant, a bleaching agent, a corrosion inhibitor, a sudsing modifier, a fluorescent whitening agent, one or more enzymes, an anti redeposition agent, a color, a fragrance, one or more additives and combinations thereof.

The present invention also include the release of active agent upon exposure to the cognate molecule or moiety that ultimately causes release upon a loss of structural integrity caused by, e.g., changes in solubility, pressure, a pH shift, a change in temperature, a temperature increase, enzymatic breakdown, diffusion and combinations thereof. The skilled artisan will also be able to be formed integrally or as a coating for controlled release or one or more layers of the active, the recognitive polymer or both. Furthermore, the polymeric recognitive network may be formed into one or more layers, each of which recognizes a different molecule, a different active or inert agent or both. The polymeric recognitive network is formed into a sphere, film, planar, semi-spherical, cylinder, rod, hemispheres, conical, hemi-cylinders and combination thereof and may also be at least partially porous. The polymeric recognitive network also may be formed into one or more layers, each of which recognizes a different molecule, and where a different active or inert agent may be contained between polymeric layers.

The present invention also includes an active agent-loaded, molecule-imprinted polymeric network that includes two or more active agent loaded, aggregated polymeric or gel nanoparticles or microparticles comprising micro- or nanovacuoles or micro- or nanopores previously imprinted with a molecule, wherein one or more pre-determined molecules bind specifically to the micro- or nanovacuoles or micro- or nanopores and contact with the molecule creates internal stresses that rupture the network at the micro- or nanovacuoles or micro- or nanopores thereby releasing one or more active agents loaded into the active agent-loaded, molecule-imprinted polymeric network.

The present invention also includes a method of making a recognitive release system by selecting one or more molecules for recognition; forming micro- or nano-vacuoles in a polymeric recognitive network about the one or more molecules; removing the molecule from the micro- or nanovacuoles or micro- or nanopores; and coating one or more active agents with a polymeric recognitive network, wherein the one or more active agents release upon contact by the polymeric recognitive network with its cognate molecule.

BRIEF DESCRIPTION OF THE DRAWINGS

For a more complete understanding of the features and advantages of the present invention, reference is now made to the detailed description of the invention along with the FIG. 1 shows the monomeric mixture used to create the present invention.

DETAILED DESCRIPTION OF THE INVENTION

Figure 1:
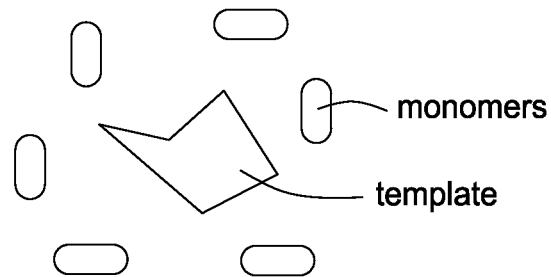

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "active agent(s)," "active ingredient(s)," "pharmaceutical ingredient(s)," and "bioactive agent(s)" are defined as drugs and/or pharmaceutically active ingredients. The present invention may be used to encapsulate, attach, bind or otherwise be used to affect the storage, stability, longevity and/or release of any of the following drugs as the pharmaceutically active agent in a composition. One or more of the following bioactive agents may be combined with one or more carriers and the present invention (which may itself be the carrier):

Analgesic anti-inflammatory agents such as, acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole, and the like.

Drugs having an action on the central nervous system, for example sedatives, hypnotics, antianxiety agents, analgesics and anesthetics, such as, chloral, buprenorphine, naloxone, haloperidol, fluphenazine, pentobarbital, phenobarbital, secobarbital, amobarbital, cydobarbital, codeine, lidocaine, tetracaine, dyclonine, dibucaine, cocaine, procaine, mepivacaine, bupivacaine, etidocaine, prilocaine, benzocaine, fentanyl, nicotine, and the like. Local anesthetics such as, benzocaine, procaine, dibucaine, lidocaine, and the like.

Antihistaminics or antiallergic agents such as, diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine, chlorpheniramine, and the like. Anti-allergenics such as, antazoline, methapyrilene, chlorpheniramine, pyrilamine, pheniramine, and the like. Decongestants such as, phenylephrine, ephedrine, naphazoline, tetrahydrozoline, and the like.

Antipyretics such as, aspirin, salicylamide, non-steroidal anti-inflammatory agents, and the like. Antimigrane agents such as, dihydroergotamine, pizotyline, and the like. Acetonide anti-inflammatory agents, such as hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like. Muscle relaxants such as, tolperisone, baclofen, dantrolene sodium, cyclobenzaprine.

Steroids such as, androgenic steriods, such as, testosterone, methyltestosterone, fluoxymesterone, estrogens such as, conjugated estrogens, esterified estrogens, estropipate, 17-β estradiol, 17-β estradiol valerate, equilin, mestranol, estrone, estriol, 17β ethinyl estradiol, diethylstilbestrol, progestational agents, such as, progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-α hydroxyprogesterone, dydrogesterone, dimethisterone, ethinylestrenol, norgestrel, demegestone, promegestone, megestrol acetate, and the like.

Respiratory agents such as, theophilline and β2-adrenergic agonists, such as, albuterol, terbutaline, metaproterenol, ritodrine, carbuterol, fenoterol, quinterenol, rimiterol, solmefamol, soterenol, tetroquinol, and the like. Sympathomimetics such as, dopamine, norepinephrine, phenylpropanolamine, phenylephrine, pseudoephedrine, amphetamine, propylhexedrine, arecoline, and the like.

Antimicrobial agents including antibacterial agents, antifungal agents, antimycotic agents and antiviral agents; tetracyclines such as, oxytetracycline, penicillins, such as, ampicillin, cephalosporins such as, cefalotin, aminoglycosides, such as, kanamycin, macrolides such as, erythromycin, chloramphenicol, iodides, nitrofrantoin, nystatin, amphotericin, fradiomycin, sulfonamides, purrolnitrin, clotrimazole, miconazole chloramphenicol, sulfacetamide, sulfamethazine, sulfadiazine, sulfamerazine, sulfamethizole and sulfisoxazole; antivirals, including idoxuridine; clarithromycin; and other anti-infectives including nitrofurazone, and the like.

Antihypertensive agents such as, clonidine, α-methyldopa, reserpine, syrosingopine, rescinnamine, cinnarizine, hydrazine, prazosin, and the like. Antihypertensive diuretics such as, chlorothiazide, hydrochlorothrazide, bendoflumethazide, trichlormethiazide, furosemide, tripamide, methylclothiazide, penfluzide, hydrothiazide, spironolactone, metolazone, and the like. Cardiotonics such as, digitalis, ubidecarenone, dopamine, and the like. Coronary vasodilators such as, organic nitrates such as, nitroglycerine, isosorbitol dinitrate, erythritol tetranitrate, and pentaerythritol tetranitrate, dipyridamole, dilazep, trapidil, trimetazidine, and the like. Vasoconstrictors such as, dihydroergotamine, dihydroergotoxine, and the like. β-blockers or antiarrhythmic agents such as, timolol pindolol, propranolol, and the like. Humoral agents such as, the prostaglandins, natural and synthetic, for example PGE1, PGE2α, and PGF2α, and the PGE1 analog misoprostol. Antispasmodics such as, atropine, methantheline, papaverine, cinnamedrine, methscopolamine, and the like.

Calcium antagonists and other circulatory organ agents, such as, aptopril, diltiazem, nifedipine, nicardipine, verapamil, bencyclane, ifenprodil tartarate, molsidomine, clonidine, prazosin, and the like. Anti-convulsants such as, nitrazepam, meprobamate, phenytoin, and the like. Agents for dizziness such as, isoprenaline, betahistine, scopolamine, and the like. Tranquilizers such as, reserprine, chlorpromazine, and antianxiety benzodiazepines such as, alprazolam, chlordiazepoxide, clorazeptate, halazepam, oxazepam, prazepam, clonazepam, flurazepam, triazolam, lorazepam, diazepam, and the like.

Antipsychotics such as, phenothiazines including thiopropazate, chlorpromazine, triflupromazine, mesoridazine, piperracetazine, thioridazine, acetophenazine, fluphenazine, perphenazine, trifluoperazine, and other major tranqulizers such as, chlorprathixene, thiothixene, haloperidol, bromperidol, loxapine, and molindone, as well as, those agents used at lower doses in the treatment of nausea, vomiting, and the like.

Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, dantrolene, and the like. Respiratory agents such as, codeine, ephedrine, isoproterenol, dextromethorphan, orciprenaline, ipratropium bromide, cromglycic acid, and the like. Non-steroidal hormones or antihormones such as, corticotropin, oxytocin, vasopressin, salivary hormone, thyroid hormone, adrenal hormone, kallikrein, insulin, oxendolone, and the like.

Vitamins such as, vitamins A, B, C, D, E and K and derivatives thereof, calciferols, mecobalamin, and the like for dermatologically use. Enzymes such as, lysozyme, urokinaze, and the like. Herb medicines or crude extracts such as, Aloe vera, and the like.

Antitumor agents such as, 5-fluorouracil and derivatives thereof, krestin, picibanil, ancitabine, cytarabine, and the like. Anti-estrogen or anti-hormone agents such as, tamoxifen or human chorionic gonadotropin, and the like. Miotics such as pilocarpine, and the like.

Cholinergic agonists such as, choline, acetylcholine, methacholine, carbachol, bethanechol, pilocarpine, muscarine, arecoline, and the like. Antimuscarinic or muscarinic cholinergic blocking agents such as, atropine, scopolamine, homatropine, methscopolamine, homatropine methylbromide, methantheline, cyclopentolate, tropicamide, propantheline, anisotropine, dicyclomine, eucatropine, and the like.

Mydriatics such as, atropine, cyclopentolate, homatropine, scopolamine, tropicamide, eucatropine, hydroxyamphetamine, and the like. Psychic energizers such as 3-(2-aminopropy)indole, 3-(2-aminobutyl)indole, and the like.

Antidepressant drugs such as, isocarboxazid, phenelzine, tranylcypromine, imipramine, amitriptyline, trimipramine, doxepin, desipramine, nortriptyline, protriptyline, amoxapine, maprotiline, trazodone, and the like.

Anti-diabetics such as, insulin, and anticancer drugs such as, tamoxifen, methotrexate, and the like.

Anorectic drugs such as, dextroamphetamine, methamphetamine, phenylpropanolamine, fenfluramine, diethylpropion, mazindol, phentermine, and the like.

Anti-malarials such as, the 4-aminoquinolines, alphaaminoquinolines, chloroquine, pyrimethamine, and the like.

Anti-ulcerative agents such as, misoprostol, omeprazole, enprostil, and the like. Antiulcer agents such as, allantoin, aldioxa, alcloxa, N-methylscopolamine methylsuflate, and the like. Antidiabetics such as insulin, and the like.

Anti-cancer agent such as, cis-platin, actinomycin D, doxorubicin, vincristine, vinblastine, etoposide, amsacrine, mitoxantrone, tenipaside, taxol, colchicine, cyclosporin A, phenothiazines or thioxantheres.

For use with vaccines, one or more antigens, such as, natural, heat-killer, inactivated, synthetic, peptides and even T cell epitopes (e.g., GADE, DAGE, MAGE, etc.) and the like.

Example therapeutic or active agents also include water soluble or poorly soluble drug of molecular weigh from 40 to 1,100 including the following: Hydrocodone, Lexapro, Vicodin, Effexor, Paxil, Wellbutrin, Bextra, Neurontin, Lipitor, Percocet, Oxycodone, Valium, Naproxen, Tramadol, Ambien, Oxycontin, Celebrex, Prednisone, Celexa, Ultracet, Protonix, Soma, Atenolol, Lisinopril, Lortab, Darvocet, Cipro, Levaquin, Ativan, Nexium, Cyclobenzaprine, Ultram, Alprazolam, Trazodone, Norvasc, Biaxin, Codeine, Clonazepam, Toprol, Zithromax, Diovan, Skelaxin, Klonopin, Lorazepam, Depakote, Diazepam, Albuterol, Topamax, Seroquel, Amoxicillin, Ritalin, Methadone, Augmentin, Zetia, Cephalexin, Prevacid, Flexeril, Synthroid, Promethazine, Phentermine, Metformin, Doxycycline, Aspirin, Remeron, Metoprolol, Amitriptyline, Advair, Ibuprofen, Hydrochlorothiazide, Crestor, Acetaminophen, Concerta, Clonidine, Norco, Elavil, Abilify, Risperdal, Mobic, Ranitidine, Lasix, Fluoxetine, Coumadin, Diclofenac, Hydroxyzine, Phenergan, Lamictal, Verapamil, Guaifenesin, Aciphex, Furosemide, Entex, Metronidazole, Carisoprodol, Propoxyphene, Digoxin, Zanaflex, Clindamycin, Trileptal, Buspar, Keflex, Bactrim, Dilantin, Flomax, Benicar, Baclofen, Endocet, Avelox, Lotrel, Inderal, Provigil, Zantac, Fentanyl, Premarin, Penicillin, Claritin, Reglan, Enalapril, Tricor, Methotrexate, Pravachol, Amiodarone, Zelnorm, Erythromycin, Tegretol, Omeprazole, and Meclizine.

The drugs mentioned above may be used in combination as required. Moreover, the above drugs may be used either in the free form or, if capable of forming salts, in the form of a salt with a suitable acid or base. If the drugs have a carboxyl group, their esters may be employed.

Examples of monomers that may be used to achieve the low or minimal swelling include: Poly(allylamine), Acrylic acid, Acrylamide, (Diethylamino)ethyl methacrylate, (Ethylamino)methacrylate, Methacrylic acid, methylmethacrylate, Triazacyclononane-copper(II) complex, 2-(methacryloyxloxy) ethyl phosphate, methacrylamide, 2-(trifluoromethyl)acrylic acid, 3-aminophenylboronic acid, poly(allylamine), o-phthalic dialdehyde, oleyl phenyl hydrogen phosphate, 4-vinylpyridine, vinylimidazole, 2-acryloilamido-2,2'-methopropane sulfonic acid, Silica, organic silanes, N-(4-vinyl)-benzyl iminodiacetic acid, Ni(II)-nitrilotriacetic acid, N-acryloyl-alanine. These monomers may be combined with one or more crosslinkers to achieve the desired low or minimal swelling upon exposure to solvent alone that include: ethylene glycol dimethacrylate, pentaerythritol triacrylate, pentaerythritol tetraacrylate, trimethylolpropane trimethacrylate, vinyl triethoxysilane, vinyl trimethoxysilane, toluene 2,4-diisocyanate, epichlorohydrin, triglycerolate diacrylate, polystyrene surface, Propylene glycol dimethacrylate, poly(ethylene glycol) n dimethacrylate, methacrylate derived silica, acrylonitrile, N,N'-dimethylacrylamide, poly(ethylene glycol) diacrylate. Examples of solvents that may be used to achieve low or minimal swelling include Acetonitrile, Acetic acid, ethanol, aqueous buffer, toluene, water, chloroform, hexane, methanol, tetrahydrofuran.

The acid mentioned above may be an organic acid, for example, methanesulfonic acid, lactic acid, tartaric acid, fumaric acid, maleic acid, acetic acid, or an inorganic acid, for example, hydrochloric acid, hydrobromic acid, phosphoric acid or sulfuric acid. The base may be an organic base, for example, ammonia, triethylamine, or an inorganic base, for example, sodium hydroxide or potassium hydroxide. The esters mentioned above may be alkyl esters, aryl esters, aralkyl esters, and the like. Also with sugar to release as a bitterness masking agent (sugar as the agent).

The bioactive may also be administered, e.g., parenterally, intraperitoneally, intraspinally, intravenously, intramuscularly, intravaginally, subcutaneously, or intracerebrally. Dispersions may be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier may be a solvent or dispersion medium containing, for example, water, ethanol, poly-ol (for example, glycerol, propylene glycol, and liquid polyethylene glycol, and the like), suitable mixtures thereof, and vegetable oils.

The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Sterile injectable solutions may be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier that contains a basic dispersion medium and the required other ingredients from those enumerated above. In the case of sterile powders for the preparation of sterile injectable solutions, the methods of preparation may include vacuum drying, spray drying, spray freezing and freeze-drying that yields a powder of the active ingredient (i.e., the therapeutic compound) plus any additional desired ingredient from a previously sterile-filtered solution thereof.

The bioactive may be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied as will be known to the skilled artisan. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a subject.

Aqueous compositions of the present invention comprise an effective amount of the nanoparticle, nanofibril or nanoshell or chemical composition of the present invention dissolved and/or dispersed in a pharmaceutically acceptable carrier and/or aqueous medium. The biological material should be extensively dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular, subcutaneous, intralesional, and/or even intraperitoneal routes. The preparation of an aqueous composition that contain an effective amount of the nanoshell composition as an active component and/or ingredient will be known to those of skill in the art in light of the present disclosure. Typically, such compositions may be prepared as injectables, either as liquid solutions and/or suspensions; solid forms suitable for using to prepare solutions and/or suspensions upon the addition of a liquid prior to injection may also be prepared; and/or the preparations may also be emulsified.

The present inventor has developed methods and techniques to form synthetic biomimetic networks, gels or polymers that will bind and respond to specific molecules, analytes or moieties. These biomimetic polymer networks, gels or polymers are advantageous because they can be tailored to bind any molecule with controlled selectivity and affinity.

There are some significant characteristics to consider in the design of a biomimetic polymer networks via a configurational biomimetic imprinting (CBIP) technique. To achieve a relatively easy on/off binding event, a non-covalent recognition process is favored. Therefore, supramolecular interactions, such as hydrogen bonding, electrostatic interactions, hydrophobic interactions, and van der Waals forces, are employed to achieve recognition. For the formation of the network, it is imperative that the functional monomers, crosslinker, and template are mutually soluble. In addition, the solvent must be chosen wisely, so that it does not interact and destabilize the self-assembled functional monomer and template.

The ability to engineer traditional polymers with specific material properties is hampered by lack of control of molecular weight, chain configuration and polymerization kinetics. Hybrid materials have been developed to preserve the bulk properties of traditional polymers while making their molecular chains look more like proteins. The elusive goal of molecular recognition in synthetic polymer systems has been reached in certain cases. Polyacrylic gels have been designed as with recognition capabilities by incorporating non-covalently crosslinked antibodies. These proteins couple the reversible swelling character of the networks with molecular recognition by only swelling in the presence of a specific antigen. The advantage of using synthetic polymeric materials based solely on proteins or peptides is the high degree of control over properties. Peptides and proteins can be coded for specific properties using a basic knowledge of inter and intrachain interactions. The present and future of biomedical materials development requires a degree of control prediction in design, synthesis and function of next generation materials. Recent work with this principle in mind has resulted in protein-based materials with properties analogous to more widely used polymers as well as new properties. These new materials have been generated with a variable degree of efficiency and complexity The development of drug delivery vehicles requires systems that respond to a specific cue in the biological environment before the release of a drug payload. This is also coupled with the desire for such new devices to otherwise maintain structural integrity and avoid clearance from the body. We have described sensitive gels with stimuli-sensitive recognition very similar to recognition in proteins. By outlining the principles developed by analyzing theoretical mechanics of heteropolymers, the underlying memory of macromolecule conformation is discovered and empirically verified. Essentially, their design includes polymerizing in the presence of target molecule, functional monomer, thermo-sensitive monomer, and end shielded post-crosslinking monomer. Some of these adsorption sites were destroyed upon gel swelling and reformed upon shrinking. Important contributions have been made describing the nature of recognition in low cross-linked systems, and it is only a matter of time when intelligent gels can recognize other types of molecules.

The present invention includes imprinted gels or chains possessing certain macromolecular architecture with binding abilities could be used as the sensing elements within analyte sensitive controlled release systems. Analyte sensitive polymer networks have been the focus of much research (mostly saccharide recognition) and have been designed in a number of ways.

Balancing pharmaceutical research for new drugs to treat human illness and disease with economic factors to minimize the cost of drug therapy has led to controlled and targeted drug delivery products. The goal of controlled drug delivery is to reduce the cost of treatment by allowing smaller, yet equally effective, dosages through a regulating device. Some drugs have very short half-lives in the human body, and large doses of these drugs are metabolized rapidly, while other drugs, such as many of the new protein drugs, are very fragile in the harsh environment inside the body. Controlled release devices can prolong the release time for the former, allowing effective dosages, and can protect sensitive drugs until the point where they are to be delivered.

In the past, drug delivery devices have been limited to systems such as tablets, capsules, powders, droplets, ointments and injections. Such systems while useful in treating some diseases have certain disadvantages: (1) they are difficult to regulate drug delivery; (2) they deliver their bioactive agent (drug) relatively fast; and (3) agent delivery is usually decreasing with time It must be noted that although the description above uses a drug as an active agent, similar problems have been observed with release of delivery of other active or bioactive agents, such as (but not limited to): pesticides, herbicides, other agricultural products, molluscicides, other marine biology products, agents that kill ticks, flees, etc., essential oils, perfumes, agents used in kitchen products, whitening agents used in laundry detergents.

More recently, systems have been developed which allow controlled release of drugs to targeted areas of the body. Some methods used for the controlled delivery of drugs include: inserts and implants, transdermal systems, oral delivery systems, nasal delivery systems, vaginal delivery systems, rectal delivery systems, ocular delivery systems and bioadhesive/mucoadhesive systems.

Most of these systems while solving the problem of prolonged delivery of active agents, are not as efficacious in applications when the patient is unwilling or unable to take the necessary drug (payload) at a specific time or specific interval. More precisely, such systems cannot control the problem of patient compliance, a significant problem in this industry.

The use of carriers sensitive to the surrounding environment, such as pH-sensitive or temperature-sensitive systems have been reported in the field. Indeed, investigators have reported methods of delivering drugs, active agents and bioactive agents in response to changes in pH or temperature of the surrounding fluid.

Clearly, such systems can improve the pattern of delivery by being triggered to release their payload when a particular pH prevails in the surrounding fluid. For example, numerous drug delivery systems have been patented where the passage from the stomach (low pH) to the upper small intestine (high pH) triggers the release of an active compound (drug). Often, such systems are accompanied by selective targeting to various tissue sites. For example, the so-called mucoadhesive drug delivery systems are based on polymeric materials which adhere to the mucin layer of a biological membrane for some length of time. The desired drug is loaded into the polymers. Once introduced to the body, the polymer carrier begins to swell, allowing the release of the drug. Because the polymer binds to the mucin layer of the membrane, the drug is released locally and is thought to be able to absorb more easily across the membrane into the bloodstream. Some possible routes of administration for mucoadhesive systems include: the nasal, ocular, buccal, gastrointestinal, vaginal and rectal areas.

There are several distinct advantages in using controlled release systems over other methods of drug delivery. First, the drug can be delivered at a relatively constant concentration. Thus, the drug concentration can be maintained at a level that is higher than the therapeutic level of the drug, but lower than the toxic level. In the case of tablets, the drug concentration steadily increases until all of the drug has been released. At this point the concentration of drug in the body may be above its toxic level. Once the drug has been released from the tablet the concentration decreases until a subsequent dose is taken. A second advantage of this type of drug delivery is that the rate and time period of delivery can be controlled depending on the properties of the polymer system.

However, the previous systems do not possess the additional advantage of intelligence of recognition of not just a change in pH or temperature, but in response to a finite concentration of an external analyte, a compound with special desirable or undesirable properties.

Most if not all of these systems, whether passive of pH- or T-sensitive have a structure that belongs to the category of hydrogels. Hydrogels are highly biocompatible which makes them appropriate for a number of pharmaceutical and medical (but also cosmetic, food and consumer) applications. In addition to drug delivery carriers, hydrogels are biomaterials used as contact lenses and scaffolds for tissue engineering applications to name only a few of the potential roles. The polymer network can contain homopolymers or copolymers with the chemical structure determining the properties of the hydrogel.

The network structure of the hydrogel can be characterized by a number of parameters. Three parameters that I will discuss here are the polymer volume fraction in the swollen state, $v_{2,s}$, the molecular weight between crosslinks, $M_c$ and the distance between crosslinks also known as the mesh size. The values for these parameters can be determined empirically or by theoretical calculations.

The polymer fraction in the swollen state is a measure of how much water the hydrogel can imbibe when placed in an aqueous environment. The ability of hydrogels to retain large amounts of water makes them similar to natural tissue and may contribute to their high biocompatibility. Both the molecular weight and distance between crosslinks give an indication of how highly crosslinked the network is. Due to the randomness involved with polymer formation, these parameters can only be given as average values throughout the hydrogel. These parameters can indicate how much space is available for diffusion in and out of the hydrogel. This value, along with the size of the agent to be delivered, will be important in determining the release kinetics of the agent from the hydrogel in drug delivery applications. The degree of swelling present in the network will affect the mesh size and therefore a physiologically-responsive hydrogel that swells when presented with certain stimuli can have different release kinetics at different sites in the body.

pH-Responsive hydrogels are composed of ionic networks and swell in response to pH changes. This swelling behavior is controlled by the ionization of the pendant groups in the network. Charged groups exhibit electrostatic repulsion that leads to imbibition of water and increased mesh size. This event also depends on the level of crosslinking present in the hydrogel. Highly crosslinked materials will not be able to swell to as high a degree as materials with lower crosslinking ratios due to decreased chain mobility. The degree to which a hydrogel network will swell is also dependent upon the ability to imbibe water. Hydrogels with hydrophilic groups can imbibe more water than those with hydrophobic groups and can therefore swell to a greater extent. The hydrophobicity/hydrophilicity of the network will therefore also have an impact on the diffusion of any compound embedded within a hydrogel network. An example of a monomer that will create an ionic hydrogel with pH-responsive swelling is methacrylic acid (MAA). When the pH of the environment is greater than the $pK_a$ of the carboxylic acid groups in MAA, they become ionized and cause interchain repulsion. The $pK_a$ of this group in poly (methacrylic acid) is approximately 4.9 making the pH shift from the stomach to upper small intestine (1.5-6) appropriate to change the ionization of the carboxyl groups. The charged groups are also hydrophilic and allow water to enter the network and continue the swelling process.

The process of ionization is reversible depending on the pH of the environment. If the MAA is grafted with another polymer capable of forming hydrogen bonds, like poly(ethylene glycol) (PEG), then hydrogen bonds can form between the chains when in the protonated state at low pH. This pH-dependant formation of hydrogen bonds provides another means by which the network exists in a compact state at low pH and a more open state at the elevated pH. Hydrogels that exhibit this activity are termed pH-responsive complexation hydrogels.

Through the use of monomers with side chains containing groups with $pK_a$ values in the range desired, a pH-responsive hydrogel could be designed much in the same manner as enteric coatings. Hydrogels can exhibit swelling to different degrees based on the intensity of the stimulus and this could be used to target release of multiple compounds at different sites. For example, if a hydrogel swelled and increased it mesh size sufficiently to release a small compound at one pH and showed increased swelling at a pH later in the gastrointestinal tract, like the colon as opposed to the small intestine, it could release a second larger agent at this location. The variability of the hydrogel delivery system in what it will respond to and how it will respond makes it an attractive candidate for numerous clinical applications including targeted drug delivery.

These hydrogels can be used for delivery of a variety of therapeutic agents. For example, previous work in our laboratory has focused on the use of hydrophilic polymer carriers for oral delivery of proteins such as insulin. The loading of proteins into the hydrogels was done by imbibition, where the polymer is swollen in a solution containing the protein and collapsed at low pH to trap the protein inside.

Recognitive Materials—Molecular Recognition. The recognition of a specific molecule out of a whole host of competing species is essential to all life processes. It is this ability that allows for the proper functioning of enzymes, antibodies, receptors, and signaling molecules. Ultimately, the design of biomaterials will include this molecular recognition ability, whether it is a smart system that recognizes only diseased cells, an implantable device with a tailored surface that does not elicit an immune response, or a sensor that can track levels of a specific compound in situ. In addition to use as biomaterials, the creation of synthetic materials with recognitive abilities will have great benefits in the areas of separations, assays, catalysis, and mass transport.

Synthetic Systems for Molecular Recognition. Undoubtedly, methods for the creation of materials with recognitive abilities similar to those shown in biological molecules such as enzymes and antibodies have been heavily sought after.

Molecular Recognition with Crosslinked Networks. By crosslinking the polymer chains, it is possible to restrict the number of conformations a given chain may adopt. In the formation of a configurationally biomimetic imprinted polymer (CBIP), interactions between a template molecule and the monomer feed molecules leads to the creation of a binding site that is subsequently locked in by polymerization and crosslinking. To date, imprinted structures have been successfully used in chromatographic applications [34-39], as sensors [40-42], and even as catalytic elements [43-46].

Wulff, et al. [34] demonstrated the first simple molecularly imprinted polymers (MIPs) utilizing monomers that had been covalently linked to the functional monomers in order to establish a proper 1:1 stoichiometric ratio. After polymerization, the template molecule was freed through lysis. This covalent technique of imprinting has several advantages including efficient use of all available functional groups and a propensity to form a more uniform binding pocket, but is restrictive in what monomers may be used. A technique later pioneered in the laboratories of Mosbach involves imprinting a freely soluble template without the use of covalent linkages [47, 48]. This technique allows for greater flexibility in the choice of functional monomers as well as template molecule. However, reaction conditions need to be more strictly controlled to maximize interaction between template and monomer molecules. In addition, a number of different binding sites may form leading to some nonspecific binding.

The molecular imprinting procedure. The production of a successfully imprinted polymer results in a material with recognitive properties. While many polymerization techniques are amenable to the imprinting procedure, most utilize a free radical technique with either thermal, ultraviolet, or redox methods providing the initiating radicals [49]. Common monomers include the methacrylate and acrylate family of molecules, acrylamides, and other vinyl derivatives as these are readily available, polymerize easily with the free radical technique, and are available with a number of functional groups [50]. In addition to monomer molecules with an array of functional groups, it is crucial to have crosslinking agents that incorporate well into the polymerization. Usually, a crosslinking agent is selected such that it has similar reactivity to the monomers used so as to form a network uniform in crosslinking density [51].

The prepolymerization mixture includes the functional monomers, crosslinking agent, initiating species, template, and solvent if desired. As free radical polymerizations are sensitive to the presence of radical scavengers such as dissolved oxygen, the mixture is first purged with an inert gas such as nitrogen. Polymerization is then initiated. As suggested by Pande et al. [28] in their work on random heteropolymers, successful imprinting is more likely to occur at lower temperatures since entropic effects are lessened, which suggests the use of either a redox or UV initiation method. However, many groups have successfully used thermal initiation, albeit at lower temperatures than normally seen for thermal polymerizations.

Following polymerization, the imprinted polymer is swollen in solvent to facilitate the removal of the template molecule. Often times before dialysis, the crosslinked material is crushed and sieved to produce particles of a given diameter in order to facilitate mass transfer. Once free of template, the MIPs are subjected to analysis of their binding ability through a variety of techniques including liquid chromatography, NMR, and microcalorimetry.

Yu and Mosbach [35] studied the influence of crosslinking density on the recognitive ability of a non-covalently formed MIP imprinted for the separation of Boc-D-Trp and Boc-L-Trp enantiomers. In their studies, it was shown that the ability to separate enantiomers decreases as the crosslinking density is decreased. This supports work done by Wulff, et al. [52] with covalently imprinted materials where in addition to a decrease in recognition, there was also a minimum amount of crosslinking needed for recognition. While increases in crosslinking density are favorable to the recognitive ability of a MIP, the resultant decrease in network mesh size may act to hinder diffusion through the network, especially limiting for the recognition of large molecules such as proteins.

Applications of molecularly imprinted materials. Historically, the main application of MIPs has been in chromatographic uses. Crosslinked recognitive materials are formed with through the imprinting process and are then crushed into particles suitable for packing into chromatographic columns [49], or used in thin layer chromatography [37]. The recognitive ability of the particles allows for affinity chromatography whereby only the compound of interest is bound by the column and all other species elute freely. This has worked especially well for the separation of enantiomers, a classically difficult separation. In 1974, Wulff, et al., [34] first suggested the formation of configurationally biomimetic imprinted polymers for the separation of D,L-glyceric acid. Since then, a significant amount of work has been focused on creating MIPs for separations, including enantiomers of Tryptophan derivatives by Yu and Mosbach [35], nicotine-like compounds by Andersson et al. [36], D- and L-phenylalinine anilide by Kriz et al. [37], penicllin G and related compounds by Cederfur et al.[38], and amino acids by Kempe and Mosbach [39].

More recently, MIPs have been employed as sensing elements due to their molecular recognition abilities. Due to the minute amounts typically bound, a highly sensitive quartz crystal microbalance (QCM) is used to determine the mass of analyte absorbed. Detection by QCM has been used by Haupt et al. [40] for the detection of R- and S-propanolol hydrochlorides, by Liang et al [41] for the detection of epinephrine, and by Hilt et al. [42] for the detection of D-glucose.

Traditionally, the design of biomaterials has focused on biocompatibility—the propensity for a material to not invoke a foreign body response upon implantation or contact in the body. Numerous studies have been done to tailor surface properties so as to not elicit an immune response. The main method has been to functionalize the surface with a hydrophilic molecule, such as grafted poly(ethylene glycol) chains, to mask the foreign surface from protein adsorption. However, it is now being recognized that molecular recognition may play an important role in future biomaterials design. Materials that show good biocompatibility are being further enhanced to include molecular recognition. Articles by Ratner [53] and by Peppas and Langer [54] discuss how building recognitive abilities into biomaterials has the potential to radically advance the field. Potential applications include: (1) materials that invoke healing pathways to rebuild tissue in the implantation area; (2) combined sensing element/controlled release device to meter and release appropriate amounts of therapeutic compounds; (3) recognitive materials specific to toxins or deleterious signaling molecules (such as angiotensin) for rapid detoxification in the blood stream; and (4) antibody or enzyme mimics for in vivo use from synthetic materials.

Researchers working towards these goals have focused on the creation of materials that are suitable for use in the body yet interact with the biomolecule of interest. Byrne et al. [55, 56] and used an imprinting technique to create hydrogels capable of binding D-glucose. This technique was later coupled with sensing technologies developed by Hilt et al. [57] to form a microsensor capable of detecting D-glucose [42]. Other glucose responsive materials have been formed by Oral and Peppas [58] utilizing star polymers and by Parmpi and Kofinas [59]. In addition to small biomolecules, Bolisay et al. prepared a configurationally biomimetic imprinted material suitable for the detection and screening of baculoviruses [60]. Molecular imprinting is well-known and can be conducted using one or more biomolecules, e.g., Acetaldehyde (metabolism byproduct); Adenine, adenosine 5V-triphosphate (ATP); Amino acid and peptide derivatives: Z-L-Tyr-OH; Z-L-Phe-OH; Z-DL-Phe-OH; Z-L-Glu-OH; Boc-L-Phe-Gly-Oet; Z-L-Ala-L-Ala-OMe; Z-L-Ala-Gly-L-Phe-OMe; Z-L-Phe-OH; Ampicillin (penicillin antibiotic); a-Amylase (enzyme); Angiotensin II (SA) (competitive inhibitor of, peptide hormone angiotensin II); Bupivacaine (anaesthetic drug); Butein (active anti-EGFR inhibitor); Caffeine (stimulant drug); Cephalexin (antibiotic drug; in a-aminocephalosporins class); Chlorphenamine (anti-histamine drug); Clenbuterol (h adrenergic blocker); Cortisone (steroid); Creatine (metabolite); Creatinine (metabolite); Cholesterol (steroid); Cholic acid sodium salt (bile acid); Carbohydrates: glucose; lactose, maltose, glucose; Glucose; Maltose; lactose; cellobiose; Carbohydrate derivatives: octyl-glucoside; p-nitrophenyl fucoside, p-nitrophenyl galactoside; Peracetylated phenyl a- and h-D-galactosides; Diazepam (i.e., valium; benzodiazepine anxiolytic drug); Enkephalin (neuropeptide); Ephedrine (stimulant drug); Epinephrine (adrenaline hormone); Estradiol (estrogenic steroid hormone); Ethynylestradiol (estrogenic steroid hormone derivative); 9-ethyladenine (nucleotide base derivative); 9-ethyladenine acetate (nucleotide base derivative); Glucose oxidase (enzyme); L-glutamine (amino acid); Histidine (N-terminal) dipeptides; Homocysteine (non-essential amino acid); Horseradish peroxidase (enzyme); Ibuprofen (non-steroidal anti-inflammatory drug); Ketoprofen (non-steroidal anti-inflammatory drug); Lysozyme (enzyme); Morphine (narcotic analgesic drug); Naproxen (non-steroidal anti-inflammatory drug); Nerve agent degradation products; (S)-nilvadipine (dihydropyridine calcium antagonists); Nucleoside base derivatives: tri-O-acetyl adenosine; tri-O-acetyl guanosine; di-O-acetyl thymidine; tri-O-acetyl cytidine; tri-O-acetyl uridine; Nucleotide base derivatives: 9-ethyladenine; 1-propyl thymine; 1-propyl cytosine; 1-cyclohexyl uracil; Oxytocin (hormone); Paracetamol (i.e., acetaminophen, analgesic); Phenylalanine (amino acid); (E)-piceatannol (active anti-EGFR inhibitor); Propanolol (h adrenergic antagonist); Quercetin (active anti-EGFR inhibitor); Ribonuclease A (enzyme); Ricin A and B Chains (toxin bean lectin); (S)-ropivacaine (anaesthetic); Scopolamine (anti-cholinergic, anti-infective; and analgesic alkaloid drug); Sulfonamides (antibiotic drug); Testosterone (steroid hormone); Tetracycline (antibiotic drug); Theophylline (Bronchodilator drug); Timolol (h adrenergic blocker); Trypsin (enzyme); Tyrosine (amino acid); Tyr-Pro-Leu-Gly-NH2 (tetrapeptide); Leu-enkephalin; Leu-enkephalin; Morphine; Morphine; Ampicillin; S-propranolol; D-phenylalanine; Adenine; 9-ethyladenine; 9-ethyladenine; 9-ethyladenine acetate; Cholesterol; Homocysteine; Trypsin; Theophylline; see, e.g., Hilt & Byne, Configurational biomimesis in drug delivery: molecular imprinting of biologically significant molecule, Advanced Drug Delivery Reviews 56 (2004) 1599-1620, relevant portions and citations incorporated herein by reference.

Protein Imprinting. The potential applications for a recognitive material capable of binding a protein are numerous, including diagnostic devices for protein assays, systems for use in immunochemistry, and separation media for extremely complicated protein mixtures. Production of such materials, however, is difficult for several reasons. First, it is known that the presence of water reduces the interactions between template and monomer since the water molecules compete for hydrogen bonds [33]. Most imprinting, therefore, is done in the presence of non-aqueous media. However, peptides and proteins are especially sensitive to differing solvent conditions and may denature in harsh solvents. Secondly, the large diameter of protein molecules may preclude the use of a densely crosslinked polymeric network since the mesh size of the network is too small to allow for efficient diffusion. It is also unclear how selective a protein imprinted material can be made, and whether subtle changes, such as the process of site directed mutagenesis, can be differentiated by these materials.

To date, several attempts have been made at creating MIPs for the recognition of oligopeptides and proteins. Shnek et al. [61] and Kempe et al. [62] focused on a surface imprinting approach whereby monomers capable of complexing a metal ion were polymerized into a MIP for with an affinity for proteins with surface exposed histidine residues. Polymers imprinted in the bulk have been prepared for the recognition of peptides by Andersson et al [63] and for the recognition of proteins by Venton and Gudipati [64]. Recently, Rachkov and Minoura [65] have demonstrated a method where only a fragment of the protein is used in the imprinting process, leading to a site that is favorable for a portion of the whole protein. This so called "epitope approach" mimics the ability of antibody molecules to recognize a portion of a protein structure.

Essential oils. Essential oils are complex mixtures of numerous compounds, they are aromatic oily liquid and can be extracted from various parts of the plants. Some of the main chemical groups found in essential oils include alcohols, aldehydes, esters, ethers, ketones, phenols and terpenes. Their use is mostly related to food as flavoring, to perfumes as fragrances and to pharmaceuticals for their functional properties. To date they are widely used as air freshener, several patents are reported dealing with their applications as deodorant, some are related to their use as good smelling insect repellent. As reported in the review proposed by Burt (2004), antimicrobial properties of some essential oils have long been recognized; in particular they have been shown to exhibit antiviral, antimycotic, antitoxigenic, antiparasitic and insecticidal properties. In the literature several works reports on their use to improve the shelf-life and safety of food and packaged food.

Controlled release systems. As reported by Peppas and Am Ende (1997), the incorporation of fragrances in polymers for the purpose of controlled release over a period of 12 or more hours has been studied. Incorporation of essential oils in polymers could lead to new and innovative products for prolonged delivery of these compounds. Peppas and Brannon-Peppas (1996) provided a wide view on papers dealing with the use of systems in which the fragrances are released from different matrices. In addition to those one, the release of linalool and linalyl acetate (the major components of aromatic lavender essential oils) from biopolymer gliadin-based nanoparticles (Duclairoir et al., 2002), the release of eucalyptus essential oil from alginate complex capsule (Chang and Dobashi, 2003) and the release of limonene from polysaccharides matrices (Secourad et al., 2003) were studied. Besides, Nakayama et al. (2003) studied the release of orange essential oils from temperature responsive membranes obtained by UV polymerization of mixture of N-isopropyl acrylamide and Polyethyleneglycole dimethacrylate. These references provide interesting information on the fragrance release mechanism but, due to the requirements and characteristics of essential oils, swelling-controlled release systems are highly desirable devices for such applications, relevant portions incorporated herein by reference.

The preparation of the above mentioned devices requires the understanding of the thermodynamic of the three-components system, consisting of the polymer, the fragrance and the liquid which is usually in contact with the device. The release of a fragrance initially embedded into the polymer matrix into the surrounding solvent is limited by several factors: the initial amount of fragrance loaded into the polymer, the solubility of the fragrance in the solvent, the equilibrium partition coefficient of the fragrance between polymer and solvent and the diffusional barrier.

The present disclosure generally relates to biomimetic polymer network compositions, methods of forming such polymer compositions, and methods of using such compositions. These compositions and have improved properties that make them useful for a variety of applications; in particular, the loading and delivery of therapeutic agents.

The biomimetic polymer networks of the present disclosure generally include a polymer network having architectures that have selective affinity for a moiety. Such biomimetic polymer networks may have shape specific cavities that match the moiety, as well as chemical groups oriented to form multiple complexation points with the moiety. In terms of selectivity, the resulting polymer networks are selective due to the particular chemistry of the binding site, the orientation and stabilization of the chemistry in a crosslinked matrix, as well as by the size and shape of the site for the template biomolecule.

In some embodiments, the biomimetic polymer networks may further comprise a moiety. Such compositions may be capable of releasing the moiety in a relatively controlled fashion. The moiety may be present on a target compound, for example, a therapeutic agent. Accordingly, the compositions and methods of the present disclosure may be used in the treatment of a disease. For example, the compositions of the present disclosure may be used as a vehicle to deliver a therapeutic agent to a subject (e.g., a human) in need thereof. The compositions of the present disclosure also may be used to form a medical device or an article. The present disclosure also provides methods of forming a biomimetic polymer network of the present disclosure.

The moiety may be any portion of a molecule recognized by a biomimetic polymer network of the present disclosure. The moiety may be covalently bound to a target compound, for example, a therapeutic agent. In this way, the moiety may be used to associate a target compound with a biomimetic polymer network of the present disclosure. The moiety should either already be present on the target compound or capable of being conjugated to a target compound. Conjugation of moieties to therapeutic agents is known in the art, for example, as disclosed in A. Wong and I. Toth, *Curr. Med. Chem.* 8:1123-36 (2001), the relevant disclosure of which is incorporated by reference. Examples of suitable moieties include, but are not limited, to sugars (e.g., glucose), carbohydrates, peptides, and functional groups. A specific example of a therapeutic agent that comprises a moiety is streptozotocin (R. R. Herr, et al., *J. Am. Chem. Soc.* 89:4808-09 (1967)), which has a glucose moiety.

In certain embodiments, the moiety is a sugar. For example, the sugar may be a monosaccharide. Monosaccharides have the chemical formula $(CH_2O)_n$ and the chemical structure $H(CHOH)_nC=O(CHOH)_mH$. If n or m is zero, it is an aldose, otherwise it is a ketose. Monosaccharides may include aldoses, trioses (e.g., glyceraldehyde), tetroses (e.g., threose), pentoses (e.g., ribose, xylose), hexoses (e.g. glucose, fructose, mannose, galactose), ketoses, trioses, tetroses, pentoses (e.g., ribulose), hexoses (e.g., fructose). Any of the L and D isomers of a sugar also may be used, although the D isomer may be more preferred for biological applications. Other examples of suitable sugars include polysaccharides. Polysaccharides have a general formula of $C_n(H_2O)_{n-1}$ where n is usually a large number up to 500. Disaccharides, such as, for example, sucrose, lactose, maltose, and the like may be used. Yet another example of suitable sugars includes oligosaccharides and low molecular weight carbohydrates (e.g., having a molecular weight no greater than about 2,000 Da). Further, each carbon atom that supports a —OH group (except for the first and last) is chiral, giving rise to a number of isomeric forms all with the same chemical formula.

Specific embodiments may use the following monosaccharides as moieties: monoses, dioses, trioses, tetroses, pentoses, aldo-pentoses, including arabinose, ribose, deoxyribose and xylose, keto-pentoses including ribulose, hexoses including aldo-hexoses such as: allose, altrose, galactose, glucose, mannose and talose, and keto-hexoses such as fructose, heptoses including keto-heptoses such as mannoheptulose and sedoheptulose, octoses such as octolose, 2-keto-3-deoxy-manno-octonateand and nonoses such as sialic acid.

Specific embodiments may use mucopolysaccharides. Mucopolysaccharides are long unbranched polysaccharides consisting of a repeating disaccharide unit. This unit consists of an N-acetyl-hexosamine and a hexose or hexuronic acid, either or both of which may be sulfated. Members of this family vary in the type of hexosamine, hexose or hexuronic acid unit they contain e.g. glucuronic acid, iduronic acid, galactose, galactosamine, and glucosamine. They also vary in the geometry of the glycosidic linkage. Specific example polysaccharides that may be used as moieties include: chondroitin sulphate, dermatan sulphate, keratan sulphate, heparan sulphate, heparin, sodium heparin, hyaluronic acid and hyaluronan.

In other embodiments, the moiety may be a lipid or a short amino acid sequence (e.g., a sequence of about twenty amino acids in length). In particular, lectins may be used as a moiety. Lectins are carbohydrate-binding proteins involved in a variety of recognition processes and exhibit considerable structural diversity. A large variability in quaternary association resulting from small alterations in essentially the same tertiary structure is a property exhibited specially by legume lectins. The strategies used by lectins to generate carbohydrate specificity include the extensive use of water bridges, post-translational modification and oligomerization. Other carbohydrate-based structures may be used as moieties may be located at http://www.chem.qmul.ac.uk/iupac/2carb/ (accessed Apr. 27, 2006), incorporated by reference herein.

In general, the compositions of the present disclosure have enhanced affinities (e.g., impart greater affinity, bound ratios greater than 1) for a chosen moiety, among other things, allowing for increased loading efficiency. Accordingly, the compositions of the present disclosure also may be used to increase the loading of a target compound or control the release rate of a target compound or both. The compositions of the present disclosure also may be used for delivery of a therapeutic agent. For example, the compositions of the present disclosure may be used as an excipient or as a vehicle for a therapeutic agent. Specifically, higher quantities of a therapeutic agent having a moiety can be loaded within the biomimetic polymer networks of the present disclosure, therefore enabling for higher doses to be loaded. The release of a moiety may be tailored to give a desired release profile, for example, for sustained release of a therapeutic agent. Thus, when the moiety is bound to a therapeutic agent, treatment with the therapeutic agent may be optimized.

The compositions of the present disclosure may be formed using configurational biomimetic imprinting. Configuration biomimetic imprinting techniques generally involve forming a prepolymerization complex between the template molecule (e.g., a moiety) and functional monomers or functional oligomers (or polymers) with specific chemical structures designed to interact with the template either by covalent chemistry or noncovalent chemistry (self-assembly) or both. Once the prepolymerization complex is formed, the polymerization reaction occurs in the presence of a crosslinking monomer and an appropriate solvent, which controls the overall polymer morphology and macroporous structure. Once the template is removed, the product is a heteropolymer network with specific recognition elements for the template molecule.

The network structure depends upon the type of monomer chemistry (i.e., anionic, cationic, neutral, amphiphilic), the association strength and number of interactions between the monomers and template molecule, the association interactions between monomers and pendent groups, the solvent type and the amount of solvent in the mixture, the reactivity ratios of the monomers, and the relative amounts of reacted monomer species in the structure. Since noncovalent forces are weaker than covalent bonds, an increased number of interactions are needed for stable binding and recognition. On a per-bond basis, noncovalent bonds are 1-3 orders of magnitude weaker. Therefore, a greater number of noncovalent bonding with matching structural orientation is needed for aqueous recognition.

A wide variety of polymers may be used to form the heteropolymer network. These include polymers produced by reaction of acrylamides and all their substituted structures including: methacrylamide, ethacrylamide, isopropyl acrylamide, etc., acrylic acid, methacrylic acid, ethacrylic acid, all alkyl acrylic acids, any dicarboxylic acid, such as crotonic acid, phthalic and terephthalic acid any tricarboxylic acid with itself another monomer of the above list (forming a copolymer), two other monomers from the above list (forming terpolymers), or three or more monomers from the above list forming higher order copolymers. The above may be in linear, branched or grafted form, the grafted chains being exclusively one polymer or copolymers of the above, ionically bound or complexed by hydrogen bonds.

The above may be crosslinked in the presence of crosslinking agents to form insoluble but swellable gels or networks, having the ability to absorb water, physiological fluids, buffers or salt solutions with final swelling as low as 1 weight % of water and as high as 99.9% water.

The above crosslinking may be achieved with ethylene glycol dimethacrylate, ethylene glycol diacrylate, ethylene glycol trimethacrylate, ethylene glycol diacrylate, ethylene glycol multi methacrylate where "multi" stands for n=4 to 200 units ethylene glycol multi acrylate where "multi" stands for n=4 to 200 units same as above but propylene glycol multi methacrylate where "multi" stands for n=1 to 200 units same as above but alkylene glycol multi methacrylate where "multi" stands for n=1 to 200 units. One may also use higher order acrylates and methacrylates including but not limited to 1,1,1 trimethylolethane trimethacrylate (TrMETrMA, Molecular Weight 324.4); 1,1,1 trimethylolpropane triacrylate (TrMPTrA, Molecular Weight 296.3); 1,1,1 trimethylolpropane trimethacrylate (TrMPTrMA, Molecular Weight 338.4); pentaerythritol triacrylate (PETrA, Molecular Weight 298.3); glycerol propoxy triacrylate (GlyPTrA, Molecular Weight 428.5); pentaerythritol tetraacrylate (PETeA, Molecular Weight 353.2); ethoxylated 1,1,1 trimethylolpropane triacrylate (ETrMPTrA, Molecular Weight 428); glycerol propoxylated triacrylate (GlyPTrA, Molecular Weight 428) and glycerol trimethacrylate (GlyTrMA, Molecular Weight 396.3). One may also use with "star polymers" or "dendrimers" with up to 72 independent chains ending in acrylates or methacrylates.

The initiator may be IRGACURE® products of the Ciba Geigy company including IRGACURE 184, IRGACURE® 379, CIBA® IRGACURE® 819, and CIBA® IRGACUREL® 250. Any other photoinitiator may also be used. The initiator may also be any peroxide including but not limited to benzoyl peroxide, cumyl peroxide, etc. or Azobis isobutyronitrile.

In some embodiments, the biomimetic polymer network of the present disclosure may be formed using a template molecule (e.g., D-glucose) and functional monomers selected to match corresponding template molecule (e.g., glucose binding protein residues, such as aspartate, glutamate, and asparagines, as well as biological mechanisms of action that involve recognition The template molecule may be added in stoichiometric amounts in regard to the functionality of the template molecule. Since solvent interaction can stabilize or destabilize binding in noncovalent systems, functional monomers may be selected based on optimizing specific noncovalent, self-assembly interactions (hydrogen bonding) with the template molecule within an aprotic solvent (e.g., dimethylsulfoxide). Such techniques are generally applicable to template molecules, in which hydrogen bonding, hydrophobic, or ionic contributions will direct recognition of the moiety. The formation of an exemplary biomimetic polymer network of the present disclosure according to the methods of the present disclosure is described below.

The multilayered mimetic structures may be constructed from a variety of coating processes, including pan coating, air-suspension coating, centrifugal extrusion, vibrational nozzle coating, supercritical fluid (SCF) based processing, fluidization (both conventional Wurster coaters such as the Glatt device) and rotating, or spray-drying.

Figure 2:
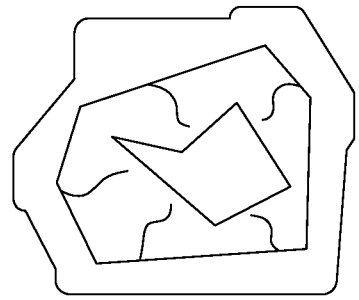
FIG. 2 shows the polymerized mixture, before the washing step.

The multilayered mimetic structures shown in FIGS. 1-2 may be constructed using a Grow Max spouted bed assisted with a draft tube and a bottom spray, also known as the Wurster configuration. The height of the bed is 535 mm and the diameter of the bed is 160 mm at the bottom and 300 mm at the top.

The bed is equipped with a sampling port to allow the microcapsule to be withdrawn and analyzed during the coating process. The bed is also equipped with a viewing window to allow the observation of the fluidizing microcapsule during the coating process. The length of the draft tube to be used is preferably 200 mm and is located 15 mm above the air distributor. The diameter of the draft tube is 70 mm. The pneumatic spray nozzle with a liquid caliber of 1.0 mm can be used to atomize the dispersion fed to the bed. A bag filter with 5 µm opening can be used to prevent the microcapsules from escaping through the top of the bed. The bag filter must be shaken frequently to prevent the microcapsule from adhering to the bag filter. The schematic diagram of the Wurster bed apparatus is shown in FIG. 2.

The advantages of the Wurster process compared to conventional fluidized bed process are: (i) the high inertia introduced in the Wurster process to circulate the particles prevents the agglomeration of the particles and (ii) the recycling profile creates a uniform coat around the particles. The circulating pattern of the particles inside a Wurster bed is made possible by a draft tube. The air inlet is concentrated just under the draft tube. This creates a high air velocity inside the draft tube and a vacuum like effect at the base of the draft tube. The particles collected under the bed are readily pulled by the air inlet into the draft tube and being carried to the top of the bed. At the exit of the draft tube, there is a sudden expansion, from the diameter of the draft tube to the diameter of the chamber. This expansion causes the particle to lose its velocity gradually and finally gravity will pull the particles back down along the wall of the chamber to the base and the process will be repeated.

Generally, a Wurster bed is equipped with a bottom spray, and hence, every time the particles pass through the based of the draft tube, latex dispersion will be sprayed on the particles. This process repeats every time the particles pass through the bottom of the draft tube, and finally, a uniform coating can be obtained. The ability to coat such small particles uniformly has broadened the applications of the Wurster process for particulate drug delivery systems.

The Wurster coating process employed in the present disclosure is very versatile and can be applied for many different materials. The process has been shown to work for many different type of cores including calcium carbonate crystal, glass beads and lactose [1-6]. Many latex dispersions have also been shown to be able to be coated using this process, such as poly(ethyl acrylate/methyl methacrylate/2-hydroxyethyl methacrylate) (P(EA/MMA/HEMA)), composite latex of core P(EAAMMA/HEMA) and P(NIPAAm) shell, crosslinked P(NIPAAm), Eudragit RS30D, L30D-55 and FS30D, and ethyl cellulose [1-6].

The Wurster coating process is a very harsh process. The process involves exposure to high temperature and high shear stress. The process requires high temperature to dry the coated microcapsules. The high shear stress is required to atomize the latex dispersion before being sprayed on the circulating microcapsules. Fortunately, the MIP nanoparticles have shown promising stability at high temperatures and high shear stresses.

One problem encountered with the coating process is the formation of a "snowman-like" structure due to agglomeration. These structures are produced by the fusion of two microcapsules. This fused structure creates weak spot along the contact point of the two microcapsules. Agglomeration prevents the formation of a single core microcapsule, which is the structure desired in this work. Several factors that affect the degree of agglomeration using the Wurster bed include: the feed rate of the latex dispersion, the flow rate of the dried air to fluidize the microcapsule and the temperature of the inlet air, the outlet air and the bed and the like.

The network structure of the layers depends upon the type of monomer chemistry (i.e., anionic, cationic, neutral, amphiphilic), the association strength and number of interactions between the monomers and template molecule, the association interactions between monomers and pendent groups, the solvent type and the amount of solvent in the mixture, the reactivity ratios of the monomers, and the relative amounts of reacted monomer species in the structure. Since noncovalent forces are weaker than covalent bonds, an increased number of interactions are needed for stable binding and recognition. On a per-bond basis, noncovalent bonds are 1-3 orders of magnitude weaker. Therefore, a greater number of noncovalent bonding with matching structural orientation is needed for aqueous recognition.

A wide variety of polymers may be used to form multilayered mimetic structures. These include polymers produced by reaction of acrylamides and all their substituted structures including: methacrylamide, ethacrylamide, isopropyl acrylamide, etc., acrylic acid, methacrylic acid, ethacrylic acid, all alkyl acrylic acids, any dicarboxylic acid, such as crotonic acid, phthalic and terephthalic acid any tricarboxylic acid with itself another monomer of the above list (forming a copolymer), two other monomers from the above list (forming terpolymers), or three or more monomers from the above list forming higher order copolymers. The above may be in linear, branched or grafted form, the grafted chains being exclusively one polymer or copolymers of the above, ionically bound or complexed by hydrogen bonds. For application in organisms, such as humans, the polymers that will have most application are those that are biocompatible, and in some cases, also biodegradable.

The above may be crosslinked in the presence of crosslinking agents to form insoluble but swell-able gels or networks, having the ability to absorb water, physiological fluids, buffers or salt solutions with final swelling as low as 1 weight % of water and as high as 99.9% water. Typically, highly crosslinked nanoparticles with high $T_g$ cannot fuse together and form films because the mobility of the polymer chain is highly restricted. This restriction on the mobility of the polymer chains prevents the polymer chains to entangle. The film formation of the hydrogel layer can be prevented by using highly crosslinked particles with high glass transition temperature, $T_g$, (as is the case with the MIP particles disclosed herein) and also by the addition of hydrophilic linear polymer chains as spacers in between the nanoparticles. On the other hand, film formation is a necessity for the skin layer. Film formation improves the rigidity and integrity of the skin layer, and hence, provides the required barrier to prevent the drug transport across the skin layer. The film formation in the skin layer can be enhanced by the addition of some plasticizers. The addition of plasticizer to the MIP may turn out to be effective in lowering the glass transition temperature of the system, and hence, enhanced the film formation of the coating layer.

Another problem with this multilayered mimetic system is the maximum size. The size is controlled by the size of the syringe because the medical counter-part of this system is designed for injectable system. The size problem can be solved by mixing several different microcapsules. For example, the size limitation would only allow the multilayered mimetic structures to have 16 layers, which would be translated to 8 bursts. If a drug delivery system requires a burst every three hours, then the system can only lasts for one day. However, if we modify the multilayered mimetic structures, so that it would rupture every 12 hours and also the outer most layer is modified into four different batches; (i) one that will rupture after 3 hours; (ii) another that will rupture after 6 hours; (iii) another after 9 hrs; and (iv) another after 12 hrs. By mixing these four different batches, the system can last for 4 instead of one day. This method of mixing made these multilayer mimetic structures to be very versatile and can easily be tailored to fit any release profiles.

In order to show controllable properties, a mathematical expression of the system an be used to predict the burst process and when each drug release will occur. This expression is derived from the force balance between the inside and outside of the seal coat layer. The microcapsule is assumed to be a perfect sphere with finite coating thickness. The MIP coat has a tensile strength, which is dependent on the molecular weight of the material. The force balance can be simplified by dividing the microcapsule into two equal hemisphere, and thus, canceling the x-component of the pressure. The pressure inside is larger than the pressure outside due to the osmotic pressure and the swelling of the hydrogel nanoparticles.

The y-component of this pressure will effectively act on the projected area of the hemisphere as represented by the left hand side of Equation 1. The tensile strength of the seal coat layer on the other hand will oppose this force along the rim microcapsule as represented by the right side of Equation 1.

$$(P_{in}-P_{out})\pi r^2 = \tau(2\pi rl) \qquad (1)$$

$P_{out}$ and $P_{in}$ are the pressures outside and inside of the hemisphere, respectively, τ is the tensile strength of the MIP coating, r is the radius of the hemisphere, and l is the thickness of the seal coat layer. This equation assumes the radius of the hemisphere is much larger than the thickness of the MIP coat. Simplifying Equation (1), the tensile strength can be expressed as a function of the net pressure, the radius of the hemisphere, and the thickness of the MIP coat layer as shown in Equation (2).

$$\tau = \frac{\Delta P r}{2l} \quad (2)$$

The tensile strength of polymers increases with increased crosslinking and ultimately reaches an asymptotic value. This can be represented as Equation (3), where A and B are constants [7, 8]. The A and B constants depended on the degree of crosslinking and the intrapolymer interactions of the polymer.

$$\tau = A - \frac{B}{\overline{M_n}} \quad (3)$$

From Equations (3) and (2) we obtain the molecular weight (crosslinking) as a function of the net pressure, the radius of the hemisphere, the thickness of the MIP coat and the constants of the material as shown in Equation (4).

$$\overline{M_n}(t) = \frac{B}{A - \frac{\Delta P r}{2l}} \quad (4)$$

Since the coating material of interest comes apart with swelling and particle separation, $\overline{M_n}$ decreases with time. The swelling disintegration of first order kinetics as described by Equation (5), where k is a rate constant.

$$\overline{M_n}(t) = \overline{M_{n_i}} e^{-kt} \quad (5)$$

Inserting Equation (5) into Equation (4) and solving for t, we may calculate the estimated lag time before the rupture process.

$$t = -\frac{\ln\left[\frac{B}{\overline{M_{n_i}}\left(A - \frac{\Delta P r}{2l}\right)}\right]}{k} \quad (6)$$

This time parameter is an important parameter that can be tailored by several approaches: (1) select materials with different disintegration kinetics resulted in different lag time by controlling the k parameter; (2) select materials with different degree of crosslinking and intrapolymer complexes thus affecting the lag time in term of the A and B parameters; (3) select material with high starting concentration and molecular weight that can prolong the lag time; (4) increase the pressure difference between the inside and outside of the multilayered mimetic structure by adding osmotic agents, such as salt and high molecular weight hydrophilic polymers that could decrease the lag time; and, (5) increase the thickness of the seal coat layer could prolong the lag time.

There are several important assumptions in this system. The net pressure difference between the inside and outside of the microcapsule is assumed to be constant throughout the degradation process. The net pressure difference is assumed constant. The thickness of the coating layer is assumed to be constant throughout the process.

EXAMPLE 1

An example of the present invention was constructed for glucose recognition followed by insulin release. The system was formed by using a core, followed by a coating of the CBIP polymer in multiple layers. The core used was glass beads (size range 63-75 µm, Sigma, St Louis, Mo.) although potato starch or other materials such as calcium carbonate crystals (size range 63-75 µm) could be used. The MIP or recognitive layer consisted of a CBIP, hydroxy propyl cellulose (HPC) as a spacer and mannitol as a binder. Triacetin was used as a plasticizer to enhance the film formation.

The MIP Hydrogel Coating. A CBIP coating was prepared by reacting 20 ml of acrylamide (Aam), 1.7 g of 2,2-dimethoxy-2-phenyl acetophenone (DMPA) as an initiator, 18 ml of dimethylsulfoxide (DMSO) as a solvent, and 8 ml of ethylene glycol dimethacrylate (EGDMA) as a crosslinking agent. The system was reacted in the presence of 10 g D-glucose. The reaction was carried out in a 100 ml glass reactor placed under a UV source (Dymax Ultraviolet Flood Cure System) and exposed to UV light with an intensity of 6.0-12.0 mW/cm$^2$ for 30 minutes to initiate the free-radical polymerization. The ensuing particles, typically of 800 nm to 20 micron size were washed repeatedly in deionized water to eliminate any unreacted monomers and to extract all the glucose. This process was completed in 4 days at 25-30 C.

The Wurster Bed Coating Process. In a suggested, typical coating study with a Wurster bed, 10 g of the core material was charged into the bed. A 5% w/w dispersion of the CBIP particles prepared before in the amount of about 40 g (2 g of CBIP solids) at a feed rate of 2.4 min/min can be sprayed on the core particle to form the 6 µm thick hydrogel layer. Then, 1 g of insulin was sprayed on the system at a feed rate of 2.4 min/min. This process created a 2 µm thickness coating.

The factors governing the flow rate of the dispersion were the solid content of the dispersion and the stickiness of the material. The lower the solid content, the lower the feed rate to the nozzle, because it took more time to dry the system. The dispersions can be fed to the spray nozzle by a peristaltic pump and atomized with a dried compressed air. The dispersion was continuously stirred during the coating process.

During all these processes, heated air (40° C.) was fed into the chamber at a flow rate of 0.25-0.75 m$^3$/min to fluidize the particles. The thickness of each layer was predetermined before the coating process. The calculation was based on the average size of the core and the thickness of the CBIP nanoparticles and insulin layers. The volume of each layer was calculated and adjusted by assuming 23% void fraction for spherical systems. The dry weight of the dispersion required to form the layers for a particles was calculated from the known densities of the dispersion. The number of the particles could be calculated by dividing the total weight of the core charged, which was 10 g by the weight of a single core. Based on these calculations, the total dry weight of each dispersion could be calculated.

Once the coating process was finished, the multilayered mimetic structure was collected and weighed to determine the yield. The multilayered mimetic structure was then sieved and the particle size distribution was analyzed. The multilayered mimetic structure was then dried under vacuum for 24 hr.

The feed rate of the latex dispersion depended on the properties of the latex itself. Tacky dispersions, with low $T_g$, required a lower feed rate. Dispersions with low solid content also required a low feed rate to allow the microcapsule to dry. The flow rate of the dried air used to fluidize the microcapsule controls the inertia of the microcapsule. High inertia could prevent the microcapsule from agglomerating. However, high inertia could also break fragile microcapsule.

The temperature of the dried air at the inlet and outlet governs the temperature of the bed. These temperatures control the rate of the drying of the microcapsule. High temperature allows the microcapsule to dry faster, and hence, allow a faster process. However, high temperature cannot be applied for a dispersion system with low $T_g$. Based on my past experience on the Wurster coating process with other materials, the operating conditions for the preparation of multilayer microcapsule in this work must be around (i) feed rate of 2.4-3.0 min/min for MIP nanoparticle dispersion; (ii) feed rate of 2.4-4.0 min/min for insulin dispersion; (iii) air flow rate of 0.25-0.75 m³/min; and (iv) air inlet temperature of 40° C.

EXAMPLE 2

A second prototype of the present invention was constructed for glucose recognition followed by insulin release. The system was formed by using a core, followed by a coating of the CBIP polymer in multiple layers. The core used was calcium carbonate crystals (size range 63-75 μm). The MIP or recognitive layer consisted of a CBIP, hydroxy propyl cellulose (HPC) as a spacer and mannitol as a binder.

A CBIP coating was prepared by reacting 14 ml of acrylic acid (AA), 1.3 g of IRGACURE® 184, 1-hydroxycyclohexyl phenyl ketone as an initiator, 18 ml of dimethylsulfoxide (DMSO) as a solvent, and 7 g of poly(ethylene glycol dimethacrylate) (PEGDMA, of PEG molecular weight of 200, 400 or 1000) as a crosslinking agent. The system was reacted in the presence of 10 g D-glucose.

The reaction was carried out in a 100 ml glass reactor placed under a UV source (Dymax Ultraviolet Flood Cure System) and exposed to UV light with an intensity of 8.0-14.0 mW/cm² for 30 minutes to initiate the free-radical polymerization. The ensuing particles, typically of 200 nm to 10 micron size were washed repeatedly in deionized water to eliminate any unreacted monomers and to extract all the glucose. This process was completed in 4 days at 25-30 C.

In a typical coating study with a Wurster bed, 10 g of the core material was charged into the bed. A 5% w/w dispersion of the CBIP partcles prepared before in the amount of about 40 g (2 g of CBIP solids) at a feed rate of 2.4 min/min can be sprayed on the core particle to form the 6 μm thick hydrogel layer. Then, 1 g of insulin was sprayed on the system at a feed rate of 2.4 min/min. This process created a 2 μm thickness coating.

EXAMPLE 3

Formulation No. 2: Recognitive and Release-triggering Systems with Multiple Recognitive Coatings for Drug Delivery The system in Example 2 can be developed into a multilayered or multicoated device where each layer contains a recognitive hydrogels prepared and applied to a core of drug by a spray coating technique (e.g., a Glatt GPCG, fluid bed coater, Glatt Air Techniques, Inc., Ramsey, N.J.). In between each coating there are annular pouches containing finely encapsulated drug particles. Each coating (layer) expands because of the osmotic effect described before. Each hydrogel coating layer is designed to rupture at preset times, thus releasing the subsequent layer of encapsulated drug particles.

Using the above technology an active agent can be released in: multiple doses of the same drug at exactly the same time intervals; multiple doses of the same drug at varying intervals (e.g., first at 10 minutes, second at 15 minutes, third at 30 minutes, fourth at 5 minutes, etc); multiple doses of two different drugs at the same or varying time intervals. These drugs maybe smaller molecular weight actives, peptides, proteins and others; multiple doses of several drugs or peptides or proteins at equal or varying intervals and/or release of an active followed by a second layer containing a sweetener to cover (mask) the bitter after taste of the first drug

EXAMPLE 4

Recognitive and Release-triggering Laminates with Multiple Recognitive Layers for Drug or Other Active Delivery A system can be developed based on the same principles as in Formulation No. 2, but in the form of thin films (laminates) stacked on top of each other. Thus, a multilayered device can be prepared where each film contains a recognitive hydrogel is prepared and applied to a core of drug by casting technique. In between each coating there are gaps containing finely encapsulated drug particles. Each laminate expands because of the osmotic effect described before. Each hydrogel laminate (film) is designed to rupture at preset times, thus releasing the subsequent layer of encapsulated drug particles.

Using the above technology an active agent can be released in: multiple doses of the same drug at exactly the same time intervals; multiple doses of the same drug at varying intervals (e.g., first at 10 minutes, second at 15 minutes, third at 30 minutes, fourth at 5 minutes, etc); multiple doses of two different drugs at the same or varying time intervals. These drugs maybe smaller molecular weight actives, peptides, proteins and others; multiple doses of several drugs or peptides or proteins at equal or varying intervals and/or release of an active followed by a second film containing a sweetener to cover (mask) the bitter after taste of the first drug.

EXAMPLE 5

Externally-triggered Multilayered Skin-adherent Films for Delivery of Essential Oils or Cosmetic Actives or Bactericides or Topical Treatment Over-the-Counter Agents A system can be developed based on the same principles as in Examples 2 and 3, but in the form of thin films (laminates) stacked on top of each other. In this case, however, the multilayered device can contain also a final thin layer of a skin adhesive polymer (e.g., pressure sensitive adhesive or poly (acrylic acid) or similar that can be used to attach the whole system to the skin. The remaining part of the device is prepared with each film containing a recognitive hydrogel prepared and applied to a core of active by a casting technique. In between each coating there are gaps containing finely encapsulated particles of essential oils, cosmetic actives, bactericides or over-the-counter agents that can be used in local skin treatment. Each laminate expands because of the osmotic effect described before. Each hydrogel laminate (film) is designed to rupture at preset times, thus releasing the subsequent layer of encapsulated agent particles.

Using the above technology an active agent can release: multiple doses of the same agent at exactly the same time intervals; multiple doses of the same agent at varying intervals (e.g., first at 10 minutes, second at 15 minutes, third at 30 minutes, fourth at 5 minutes, etc); multiple doses of two different agents (e.g., a perfume compound and a bactericide) at the same or varying time intervals; multiple doses of several drugs agents at equal or varying intervals.

EXAMPLE 6

Sweat-triggered Multilayered Skin-adherent Films for Delivery of Essential Oils or Cosmetic Actives A system developed on principles similar to those of Examples 2-4, but in the form of multiple thin films (laminates) triggered by actives produced by the human sweating process and releasing actives. Such triggering molecules will be epinephrine and related compounds. The multilayered device will also contain a final thin layer of a skin adhesive polymer (e.g., pressure sensitive adhesive or poly(acrylic acid) or similar) that can be used to attach the whole system to the skin.

The remaining part of the device is prepared with each film containing an epinephrine-imprinted, recognitive hydrogel prepared and applied to a core of active by a casting technique. In between each coating there are gaps containing finely encapsulated particles of essential oils, cosmetic actives, bactericides or over-the-counter agents that can be used in local skin treatment. Each laminate expands because of the osmotic effect described before. Each hydrogel laminate (film) is designed to rupture at preset times, thus releasing the subsequent layer of encapsulated agent particles.

Using the above technology we can release: multiple doses of the same agent at exactly the same time intervals; multiple doses of the same agent at varying intervals (e.g., first at 10 minutes, second at 15 minutes, third at 30 minutes, fourth at 5 minutes, etc); multiple doses of two different agents (e.g., a perfume compound and a bactericide) at the same or varying time intervals; and multiple doses of several drugs agents at equal or varying intervals.

EXAMPLE 7

Sweat-triggered Multilayered Nanoparticles for Delivery of Essential Oils or Cosmetic Actives A system developed on principles similar to those of Examples 2-4, but in the form of multiple nanoparticles in the form of devices triggered by actives produced by the human sweating process and releasing actives. Such triggering molecules will be epinephrine and related compounds. Such systems can be applied as a dry powder and can release at various times, as late as 8 hours after application. They may contain expensive perfume, essential oils, bactericides, etc.

EXAMPLE 8

Sweat-triggered Multilayered Skin-adherent Films for Delivery of Oils, Lipids or Creams Delivery of highly hydrophobic active agents using the MS/UT technology (after initial recognition) is extremely difficult as the lipidic structures are extremely difficult to penetrate through hydrophilic gels. However, with the present technology a multivariate system can be prepared, where the encapsulated nanoparticles are wholly covered by hydrophobic coatings and reside in the space between consecutive layers of epinephrine-recognitive hydrogel films. A system was in the form of multiple thin films (laminates) triggered by actives produced by the human sweating process and releasing actives. Such triggering molecules will be epinephrine and related compounds. The multilayered device may also contain a final thin layer of a skin adhesive polymer (e.g., pressure sensitive adhesive or poly(acrylic acid) or similar) that can be used to attach the whole system to the skin.

The remaining part of the device is prepared with each film containing an epinephrine-imprinted, recognitive hydrogel prepared and applied to a core of active by a casting technique. In between each coating there are gaps containing finely encapsulated particles of creams that can be used in local skin treatment. Each laminate expands because of the osmotic effect described before. Each hydrogel laminate (film) is designed to rupture at preset times, thus releasing the subsequent layer of encapsulated agent particles.

The remaining part of the device is prepared with each film containing an epinephrine-imprinted, recognitive hydrogel prepared and applied to a core of active by a casting technique. In between each coating there are gaps containing finely encapsulated particles of creams that can be used in local skin treatment. Each laminate expands because of the osmotic effect described before. Each hydrogel laminate (film) is designed to rupture at preset times, thus releasing the subsequent layer of encapsulated agent particles.

EXAMPLE 9

Preparation of Recognitive Systems

Preparation of Films from Recognitive Polymers. The configurational biomimetic imprinted polymer (CBIP) recognitive films prepared in this work included a crosslinked copolymer of methacrylic acid (MAA 99%, inhibited with 100-250 ppm HQ, Sigma-Aldrich, St. Louis, Mo.) and ethylene glycol dimethacrylate (EGDMA, stabilized, 98%, Acros Organics, N.J.). The reaction mixture was imprinted with D-glucose (A.C.S. reagent, Aldrich Chemical Co., Milwaukee, Wis.). The monomers were photopolymerized in the presence of UV light with 2,2-dimethoxy-2-phenylacetophenone (DMPA, 99%, Acros Organics) used as the free-radical initiator. All solvents were of analytical grade.

MAA (10% w/w) and D-glucose (5% w/w) were added to a solution comprised of a 3:1 ratio of ethanol to water (by volume) and were sonicated for 20 minutes to evenly disperse the components. To this mixture, EGDMA (84% w/w) and DMPA (1% w/w) were added and mixed by mechanical shaking. This mixture was then purged with $N_2$ in an oxygen-free environment (e.g., a sealed glove box) for 30 minutes. After purging, the mixture was loaded into a polymerization chamber (made from two 75×50×1 mm microscope slides with a 200µ Teflon spacer placed in between, bound with binder clips around the edge) and polymerized under UV light (at 15 mW/cm2) for 15-20 minutes. The resulting films were then removed from the glove box and washed with Milli-Q DI-water for 24-48 hours (with the water being changed every 24 hours), after which they were removed and dried in a drying oven (with desiccant) for 24 hours. The resulting films were then stored at room temperature for observation.

Preparation of Control Samples. The control samples (non-imprinted polymer films) were prepared using precisely the same protocol as above, except for the absence of D-glucose from the mixture (i.e., no glucose was added).

Figure 3:
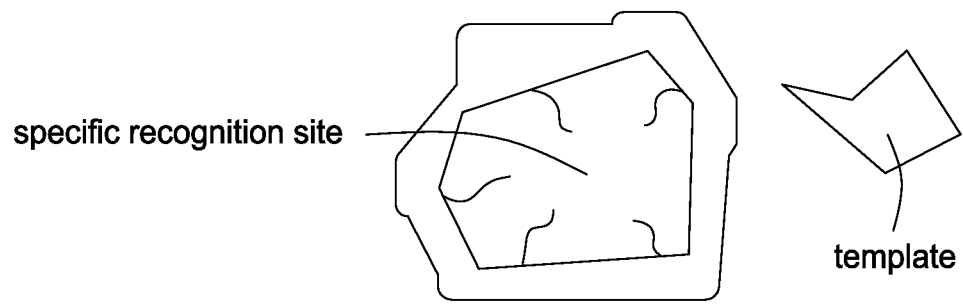
FIG. 3 shows the polymer after washing in which the template has been removed and the specific recognition site remains within the polymer.

Configurational Biomimetic Imprinting in the Presence of Glucose. The biomedical applications for the novel systems are far reaching due to a unique development in the field known as molecular imprinting, a concept upon which our CBIP systems are based. Molecular recognition via imprinting is accomplished by having a certain template molecule (in our case, glucose) dispersed between the various monomers during the process of polymerization (FIG. 1). The monomers proceed to polymerize as usual, while the specific template is imprinted directly within the polymer network (FIG. 2). The polymer films are then washed, thus removing the template molecule (e.g., glucose) and leaving behind a chemically stereospecific site where the template molecule was once part of the network (FIG. 3). When the film is subsequently dried, nanovacuoles are present, while the polymer's physical characteristics change (notably a decrease in overall size). When glucose is reintroduced to the system, the attachment of the molecule to the stereospecific site causes a mechanical stress in the local region that will eventually lead to rupturing; it is this template-specific recognition/rupture/delivery that we seek to exploit in the form of novel drug delivery systems. The templates used in this type of recognition can be extended to almost any molecule; further investigation will reveal new applications for this technique.

Sample Preparation. After numerous different procedures or "recipes" were performed, a general procedure was selected. There were many variations to the results of each recipe and method. At present time, not all factors have been tested. Samples prepared with low amounts of EGDMA as a crosslinker showed significant differences from those films made with at least 25 wt % crosslinker (the preferred ones). The crosslinker must be present in a high enough amount to hold the copolymer together. This was noticed from the films which remained fluid or tacky and glutinous after the polymerization time ended. Different procedures were also followed with different amounts of ethanol and water. Adding more ethanol to the recipe seemed to help the films polymerize more but also sometimes made the films turn out white.

It must be noted though, that it is necessary to do also studies at lower crosslinking ratios because of the ability to imprint larger proteins in these systems. It is particularly necessary to appreciate that such systems will be important for consumer applications where added lipids will be necessary.

The polymerization time (under the UV lamp in the glove box) made a difference as to how rigid and continuous each film was. The first samples were prepared by polymerization for approximately 15 to 20 minutes according to the protocol described in Example 2. But many of the recognitive and non-recognitive films polymerized under these conditions were still "sticky". Some films were polymerized for longer amounts of time (up to 60 minutes).

There were other laboratory procedures that were followed before complete polymerization of the films. First, the monomer solution was sonicated for at least 20 minutes before adding EGDMA and DMPA to ensure a mixture. Once the EGDMA and DMPA were added and sonicated again for a few seconds.

Characterization. Characterization of the prepared films was done by swelling studies, optical and electron microscopy, FTIR analysis and differential scanning calorimetry. We will report here only what has been completed already. Microparticles and continuous films were observed under polarized light, normal light, and with fluorescein isothiocyanate—(FITC)—glucose under fluorescent light. The swelling of the films was studied in solutions of different glucose concentrations and DI water.

Swelling Studies. The purpose of these studies was to examine the recognitive and swelling characteristics of all recognitive samples. This was done because of numerous questions received by Mimetic Solutions as to the ability of the recognitive samples to recognize their templates fast and rupture as a result of the stresses created.

For each swelling study, the recognitive continuous films were cut into disks or squares between 0.13 mm and 0.22 mm thick. The disks were cut with a cork-borer with a radius of approximately 8 mm; the squares were cut with a razor blade to approximately $9 \times 9$ mm$^2$. Before a swelling study, the weight, thickness, and dimensions of each sample were recorded. The disks or squares were then immersed into beakers with either DI water, 100 mg/dL glucose solution, 150 mg/dL glucose solution, or 200 mg/dL glucose solution. The DI water was used as a control to see if the disks and squares would swell without glucose present. It was found that the samples exposed to DI water should not swell as much as the samples placed in a glucose solution.

Every ten minutes, samples were removed by tweezers, blotted gently with a wipe, and weighed. The total time that each sample was out of solution was roughly one minute. All studies were done at 37 C. In addition, the pH of each solution was measured.

In all studies, the amount of penetrant uptake was calculated by subtracting the dry weight of sample (polymer) from a later weight and then dividing by the dry weight of sample. These values are a clear indication of a fast uptake by the recognitive system. These values were plotted as a function of time and as a function of square root of time (see FIGS. 4-7). These Figures show that glucose is recognized by the recognitive samples, leading to fast binding. A very fast recognition process is observed with glucose (100 mg/dl solution) with subsequent saturation of the binding sites and reduction of the water uptake until a constant value is obtained, almost the same as for pure water absorption. Scientifically, this phenomenon can be interpreted in a similar way as the action of solid catalysts. Once the active sites are occupied, no further reaction can take place.

Numerous studies of recognition at higher glucose levels (e.g., 150 mg/dL and 200 mg/dL) indicated that these samples fractured within a few minutes (typically 13-20 minutes for thin films) after exposure to the solutions. Indeed, graphs of penetrant uptake (1) versus time cannot be presented as the weight decreased after being the samples were placed in solution because of the rupture or cracking.

Figure 4:
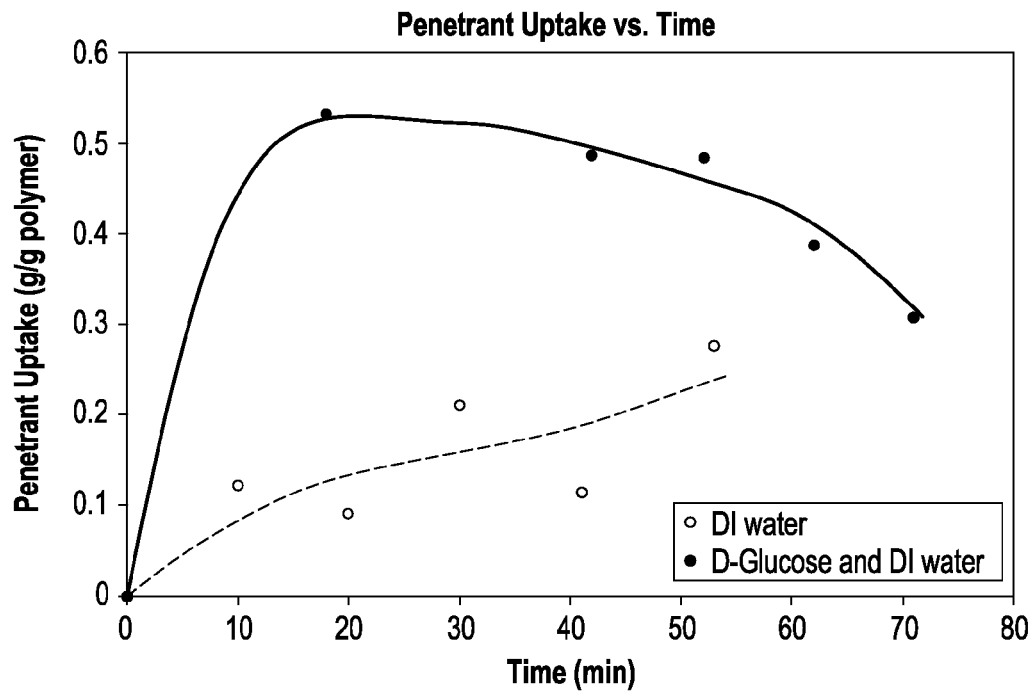
FIG. 4 is a graph that shows penetrant uptake of a recognitive polymer continuous films over time. The data points are amount of penetrant uptake in Milli-Q deionized water (DI water) and 100 mg/dL D-glucose and DI water. The films were cut into disks 8 mm in diameter and 0.12 mm thick; the initial weights were approximately 6 mg each. Measurements were taken every 10 minutes.

FIG. 4 is a graph that shows the penetrant uptake of recognitive polymer continuous films over time. The data points are the amount of penetrant uptake in Milli-Q deionized water (DI water) versus 100 mg/dL D-glucose in DI water. The films were cut into disks 8 mm in diameter and 0.12 mm thick; the initial weights were approximately 6 mg each. Measurements were taken every 10 minutes.

Figure 5:
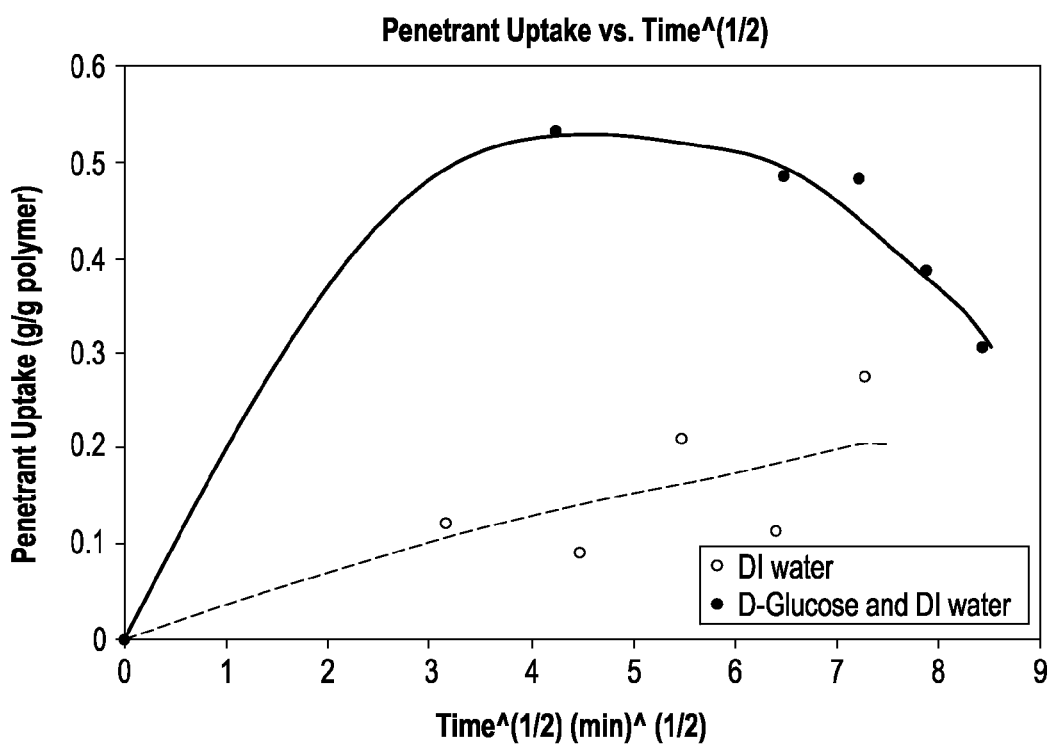
FIG. 5 is a graph that shows penetrant uptake of a recognitive polymer continuous film versus the square root of time. The data points are amount of penetrant uptake in Milli-Q deionized water (DI water) and 100 mg/dL D-glucose and DI water. The films were cut into disks 8 mm in diameter and 0.12 mm thick; the weights were approximately 6 mg each. Measurements were taken every 10 minutes.

FIG. 5 is a graph that shows the penetrant uptake of a recognitive polymer continuous film versus the square root of time. The data points are amount of penetrant uptake in Milli-Q deionized water (DI water) versus 100 mg/dL D-glucose in DI water. The films were cut into disks 8 mm in diameter and 0.12 mm thick; the weights were approximately 6 mg each. Measurements were taken every 10 minutes.

Figure 6:
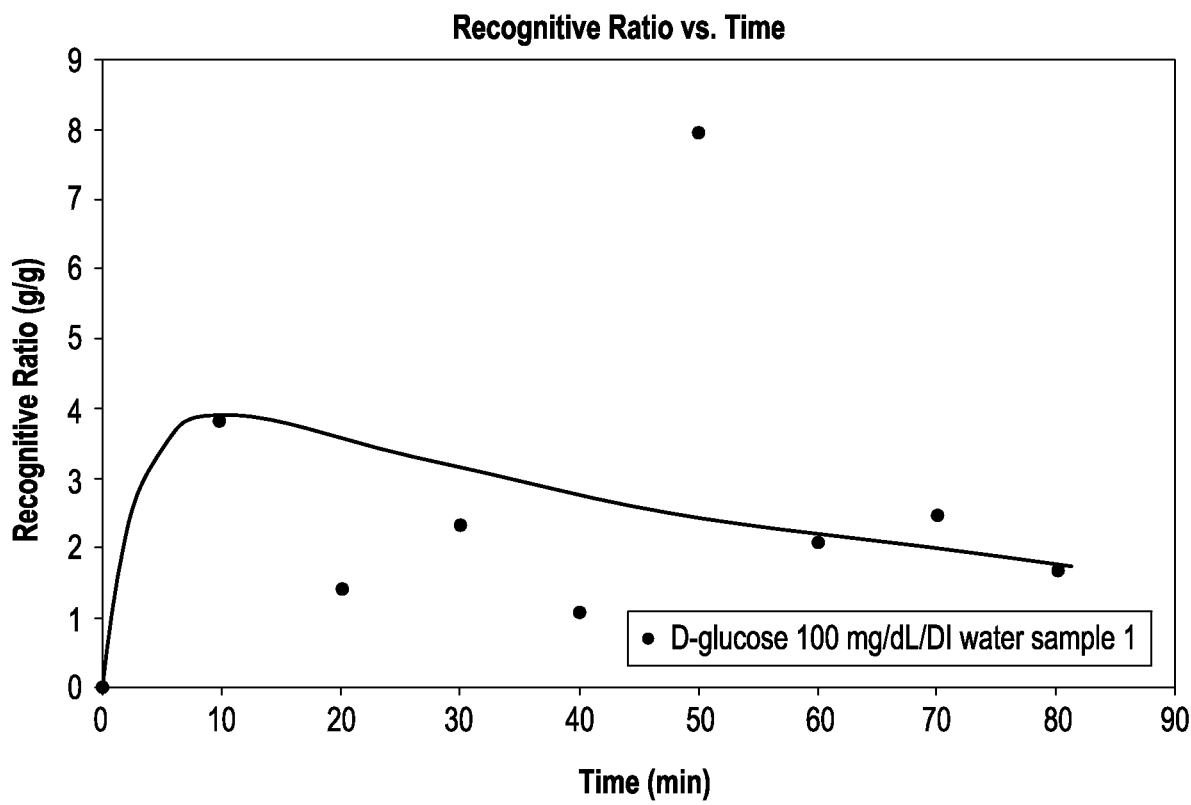
FIG. 6 is a graph that shows the recognitive ratio of configurational biomimetic imprinted polymers (CBIP) in the presence of 100 mg per dL deionized water compared to continuous films in the presence of deionized water. The films were cut into squares approximately 9 mm by 9 mm and 0.22 mm thick. The penetrant uptake amount was obtained from measurements of mass every 10 minutes once the squares were placed in the solutions of either deionized Water or glucose solution with 100 mg D-glucose per dL deionized water. The ratio is the amount of penetrant uptake in the glucose solution to amount of penetrant uptake in deionized water.
Figure 7:
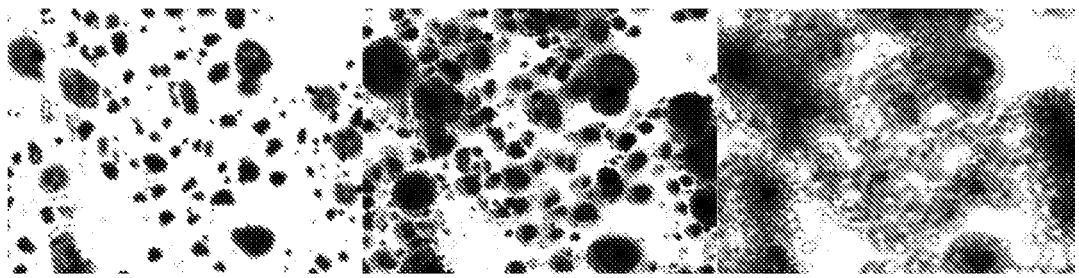
FIG. 7 shows a Glucose CBIP (5/31 mixture) after exposure to 100 mg/dL glucose -water (60 seconds pass between each frame). (50× objective). [0026]

FIG. 6 is a graph that shows the recognitive ratio of configurational biomimetic imprinted polymers (CBIP) in the presence of 100 mg per dL deionized water compared to continuous films in the presence of deionized water. The films were cut into squares approximately 9 mm by 9 mm and 0.22 mm thick. The penetrant uptake amount was obtained from measurements of mass every 10 minutes once the squares were placed in the solutions of either deionized Water or glucose solution with 100 mg D-glucose per dL deionized water. The ratio is amount of penetrant uptake in the glucose solution to amount of penetrant uptake in deionized water.

Observation of Swelling and Recognitive Processes. A large number of the recognitive films were crushed using mortar and pestle or cut into 8 mm disks using a cork borer in order to observe their response to glucose solutions under the microscope. The swelling behavior of different CBIP and NIP (control) films was observed in DI water, and solutions of 100 mg/dL glucose, 150 mg/dL glucose, 200 mg/dL glucose, 300 mg/dL, FITC-glucose, and trypan blue. The samples were tested under normal light, polarized light, and fluorescent light (when using FITC-glucose). The particles (approximately 100-300 micrometers) were placed on a microscope slide and pictures were taken before any solution was added. Then using either a spatula or a pipette, a drop or two of solution were placed on the samples. Effort was made to avoid capillarity effects. Still photographs were taken in succession to form videos. The purpose of using a trypan blue solution was to observe the liquid front movement into the particles or films.

Observations Without Polarization. Swelling of particles and films was difficult to observe without polarized light. In general, the particles tended to agglomerate together when in solution, which could sometimes be mistaken for swelling.

Figure 8:
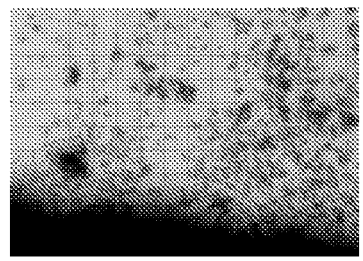
FIG. 8 shows a nebula of disintegrated particles from a porous film exposed to 100 mg/dL glucose-water (5× objective).

FIG. 8 shows typical recognitive response and swelling behavior of particles within a few seconds from exposure to the glucose-containing solution. After one minute, the particles have started recognizing glucose, which creates internal stresses. The third panel of FIG. 8 clearly shows the swollen particles that have formed from the larger particles due to rupture.

Figure 9:
FIG. 9 shows the Stress lines seen on a polymer film 30 sec after addition of glucose. (5× objective).

FIG. 9 shows a very large number of particles produced by the same recognitive process but using films containing a porosigen (see below) to produce large pores within the recognitive polymer.

Figure 10:
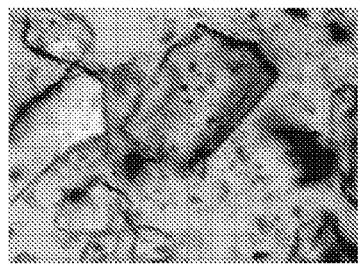
FIG. 10 shows a section of a glucose-CBIP film immersed in a glucose solution and seen breaking at a first time point (10× objective).

FIG. 10 show stress lines formed during the first few seconds after addition of a glucose solution to a recognitive film produced as described above. Clearly, these observed stress lines indicate the effect of glucose on the CBIP system. These lines cannot be observed in similar films exposed just to water or in NIP films (neat films, not imprinted).

Figure 11:
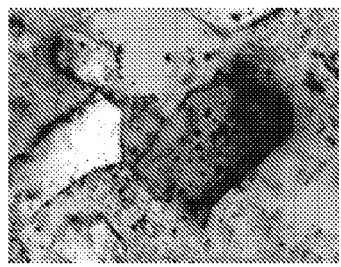
FIG. 11 shows a section of a glucose-CBIP film immersed in a glucose solution and seen breaking at a second time point (10× objective).

FIG. 11 shows a typical sequence of stills from a video of the recognition/swelling and rupture of a thin film of a glucose-recognitive CBIP film exposed to glucose. Clearly, the film ruptures with continuous extended cracks. This is a fundamental difference over the rupture of CBIP particles (FIG. 8) that occurs in the form on numerous irregularly shaped particles.

Figure 12:
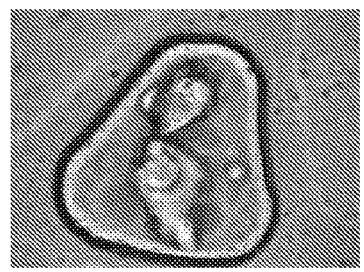
FIG. 12 shows a Trypan Blue dyed water-front moving in toward a CBIP particle.

Observations of Moving Fronts with Dyes. Trypan blue was used in the recognitive solution to better delineate the fronts moving into all the particles and to help us observe the recognition due to the motion of the glucose solution and associated swelling of particles and continuous films. FIG. 12 shows one such process with a clear indication of the position of glucose fronts (darker area) as they penetrate in the microparticles. This is a rather simple technique to verify front positions although it is less useful to identify stress lines (the clear indication of glucose action on the samples). This was achieved with the techniques described below.

Observation of Recognitive Processes Using Polarized Light.

Polymer stresses as a result of recognition processes, polymer crazing, cracking or dissolution involve glucose or solvent transport into the polymer followed by actual rupture and perhaps dissolution of the latter. Numerous study techniques have been reported to study polymer stresses and dissolution. The simplest method is a gravimetric technique where polymer specimens are immersed in a solvent and removed after fixed time intervals. These specimens are then dried to remove residual solvent and the thickness of the remaining film is measured. Thus, the temporal evolution of the thickness is also obtained. Though simple, this method is tedious and almost impossible to use here.

Laser interferometry has been used to measure the polymer dissolution rate of thin films. The technique has found applicability especially in following the dissolution of microlithographic masking layers. In this study, a recognitive polymer coated on a silicon wafer is placed in a solvent. When a laser beam impinges upon the polymer surface, it splits into two beams: one is reflected by the surface and the other penetrates the thin polymer film and is reflected by the silicon wafer. The two beams interfere with each other, providing a measure of the change of the polymer film thickness as a function of time. This technique is also limited to those polymers that give a negligible gel layer because good interference cannot be obtained if the gel layer thickness is significant.

Differential refractometry can also be used to measure the polymer dissolution rate. In this study, a polymer sample is immersed in a glucose solution in a special container, equipped with a differential refractometer and an agitator. Polymer cracking and dissolution are followed by measuring the refractive index of the solution. Using this method, it is also possible to measure induction times, which are the times necessary for a build-up of a swollen surface layer. The differential refractometry technique can be used even in the presence of gel layers. However the thickness of the gel layer cannot be measured simultaneously.

To measure both the recognition and CBIP polymer dissolution rate and the gel layer thickness as well as to investigate polymer morphology during dissolution, techniques using optical microscopy have been used. The apparatus consists of an optical microscope and a sample cell containing a CBIP polymer sample engulfed by a matrix inert to the solvent and sandwiched between two glass slides. As the contrast between the different layers was usually poor, dyes are resorted to in the glucose solution.

To improve the contrast between the different layers, we designed an optical microscopy apparatus with modifications in the sample cell and the optical design, which obviated the need for the dye tracer. By changing the angle of illumination of the sample, we found that the contrast achieved between the different layers in the recognitive, cracking/rupturing or dissolving polymer was sufficient for their resolution. The optimum angle of illumination depended on the refractive indices of the glucose solution and the CBIP polymer, and also on the sample thickness. The sample cell design was also modified to improve the flow rate control and to allow greater precision in measuring the motions of the boundaries of the different layers.

Figure 13:
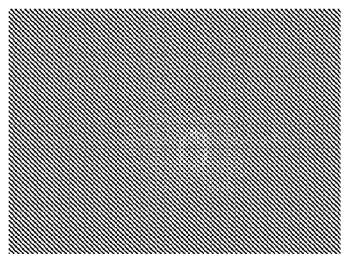
FIG. 13 shows a CBIP particle in glucose-water viewed through two polarized lenses. Soft image means no significant stresses in the surface of the particle (the image is mostly dark due to the lack of reflection).
Figure 14:
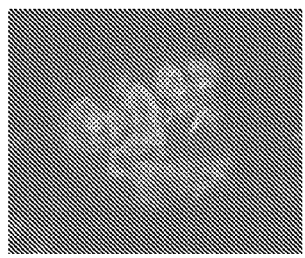
FIG. 14 shows a CBIP polymer particle viewed through two polarized lenses. The reflective areas indicate changes in surface morphology due to mechanical stresses.

Thus, techniques using optical microscopy are good tools for observing the different layers as well as the possible crazing or cracking at the interface of a dissolving CBIP polymer. Under polarized light, glucose-sensitive stress lines and fractures appear in the presence of a glucose solution. When the polarizer and analyzer of the polarized microscope are crossed, the only light that can be seen is from birefringence (as shown in FIG. 13 from a single particle before it has started rupturing). This birefringence is the result of stress lines caused by glucose expanding the polymer particles. A typical sample showing birefringence is seen in FIG. 14 that presents a CBIP particle as it has started to rupture and crack. In this particular study, the ruptured particles appeared after 2 min and 55 sec.

Figure 15:
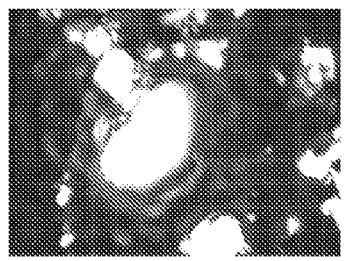
FIG. 15 shows a glucose CBIP exposed to fluorescent glucose; the intake of the glucose is indicated by the brightly lit areas (10× objective).
Figure 16:
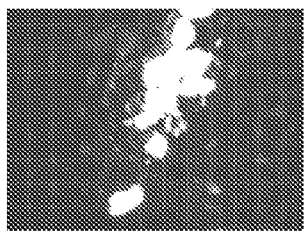
FIG. 16 shows a glucose CBIP exposed to fluorescent glucose; breakage is apparent here (10× objective).

Observation of Recognitive Processes Using Fluorescent Markers. FITC-glucose provided one of the best ways to observe the recognitive process as well as the swelling of the particles and continuous films, because fluorescence can be readily detected. We have not completed studies in fluorescent light, but FIGS. 15 and 16 show some of the results. The brightness of the particles corresponds to the stresses and swelling caused by the FITC-glucose (FIG. 15). The swelling generally occurred within 3-5 minutes after contact with the glucose solution. Recognition and stress development was very much dependant on particle size. Particle of 10-15 microns were recognitive within 10 seconds!

Particles appeared to burst in the presence of FITC-glucose (FIG. 16). These bursts could probably be FITC-glucose solution "bubbles" bursting within the particles after they have had enough stress from surrounding solution. This proves that the recognition of glucose does in fact lead to enough mechanical stress to cause the recognitive particles to break apart. This is exactly what the ultimate goal of these studies is: to have a recognitive layer with a glucose template that will burst upon recognition of an abnormal level of glucose and release insulin.

Figure 17:
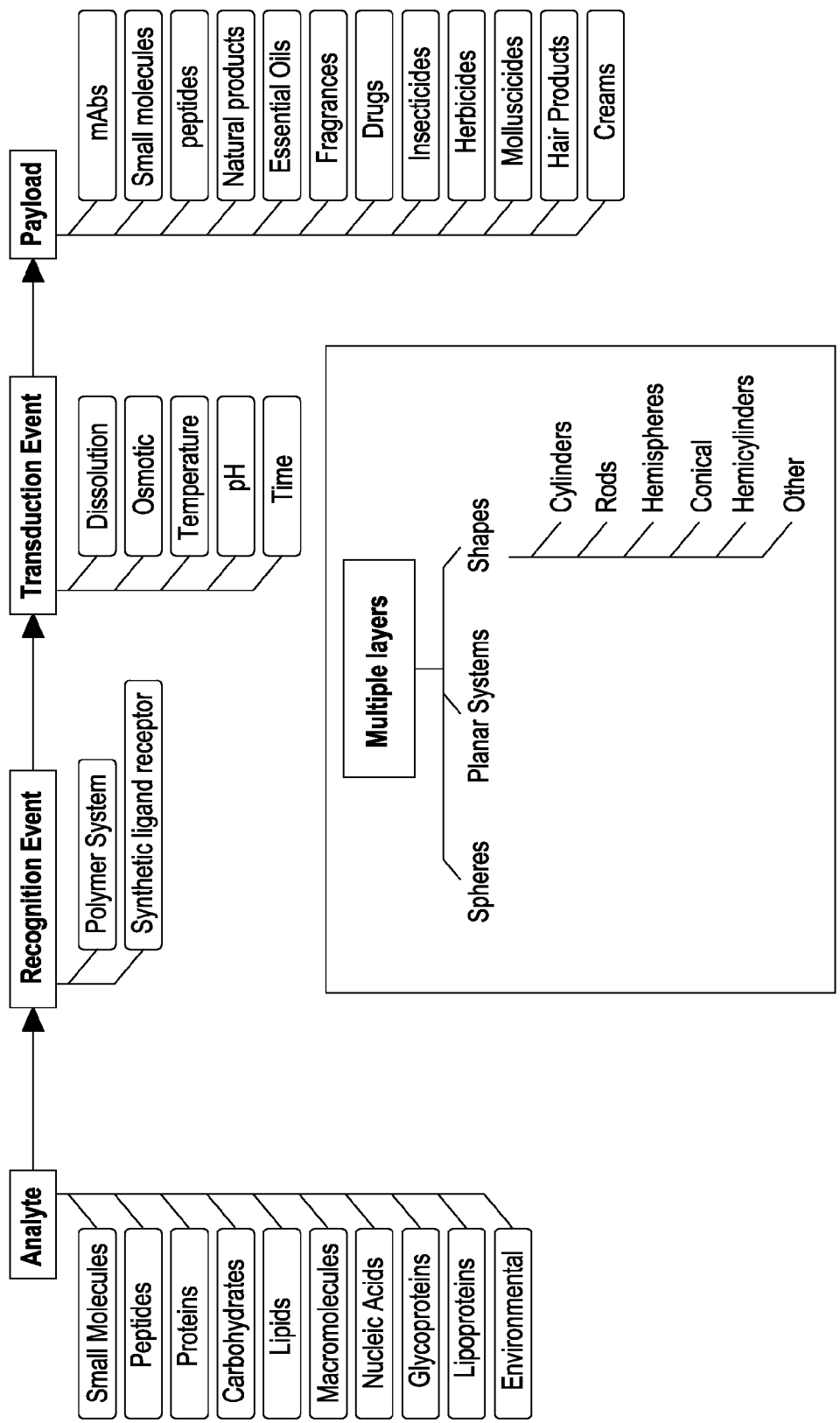
FIG. 17 shows the optional combinations for the various embodiments of the present invention in which the optional analyte, recognition and transduction events and payloads.

FIG. 17 shows, at a high level, the basic combinations of the present invention. As the skilled artisan will appreciate, the molecule that is used to form the micro or nanovacuoles (shown here as the analyte) can be any of a wide variety of molecules (or combinations thereof) that can be recognized by the polymeric network. Upon exposure the analyte (i.e., the recognition event), a polymeric transduction event occurs in which one or more of the listed forces (or even additional forces) trigger a dissociation, degradation, decomposition or otherwise reduce the structural integrity of the polymeric network, thereby triggering the delivery of a payload. One example of a payload may even be a lower or subsequent layer of polymeric network, which may also include a core on which the layers may be disposed.

Figure 18:
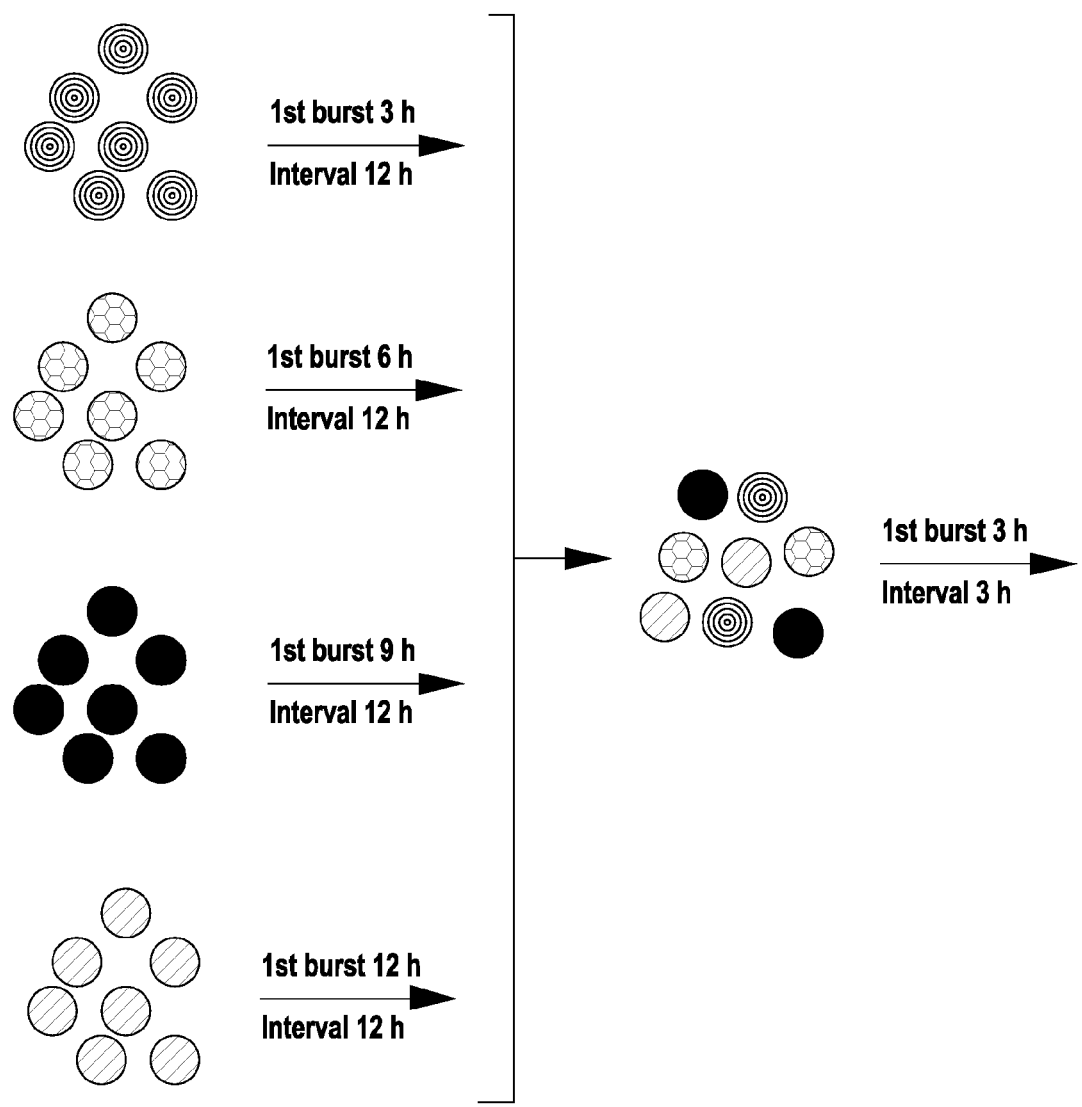
FIG. 18 is a diagram that shows mixing multilayered mimetic structures with different release profiles that allows the system to be tailored to fit any release profiles. Mixing four different microcapsules allowed the system to rupture every 3 h for 4 days instead of a system that ruptured every 12 h for 4 days or a system that ruptured every 3 h for one day.

FIG. 18 is a diagram that shows mixing multilayered mimetic structures with different release profiles that allows the system to be tailored to fit any release profiles. Mixing four different microcapsules allowed the system to rupture every 3 h for 4 days instead of a system that ruptured every 12 h for 4 days or a system that ruptured every 3 h for one day.

EXAMPLE 10

Limited Swelling of the Recognitive Polymeric Network in Solvent Alone

The configurational biomimetic imprinted polymer (CBIP) recognitive films prepared in this work included a crosslinked copolymer of 4.0 ml water, 4.5 ml ethanol, 60 mg glucose, 0.42 g MAA, 3.1 g TEGDMA, optionally a few drops of ethanol. Next, 50 mg DMPA was added. The solution is degassed for 4 minutes and loaded. The polymer is formed by UV irradiation for 5 minutes. The polymer opaque while film is washed with water and removed from the slide. Washing is as described hereinabove.

Figure 19:
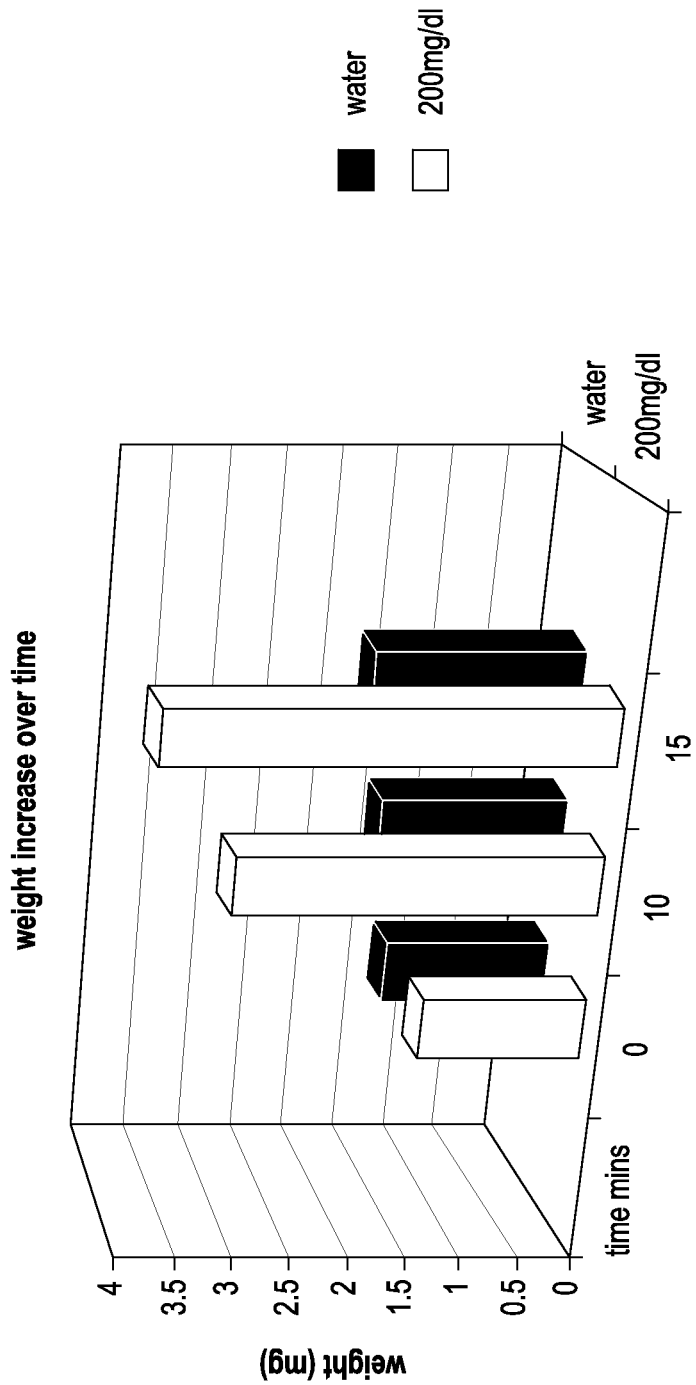
FIG. 19 shows glucose/water uptake of a CBIP.

FIG. 19 shows glucose/water uptake in which glucose solution caused the samples to fall apart quite quickly. The graph shows that the polymer swelled between 5-15 percent (±3%) in the presence of a solvent (water) alone. Upon exposure to the solvent and the analyte the polymeric network burst to release the payload. At lower glucose concentrations it is expected that the release can run the time course to equilibrium.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue studyation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. E. S. Golub and D. R. Green, Immunology: A Synthesis. 1991, Sunderland, MA: Sinauer Assoc.
2. F. Breinl and F. Haurowitz, Chemical Investigation of the Precipitate from Hemoglobin and Anti-hemoglobin Serum and Remarks on the Nature of Antibodies. Z. Physiol. Chem., 1930. 192: p. 45.
3. L. Pauling, A Theory of the Structure and Process of Formation of Antibodies. J. Am. Chem. Soc., 1940. 62: p. 2643-2657.
4. N. K. Jerne, The Natural Selection Theory of Antibody Formation. Proc. Natl. Acad. Sci. USA, 1955. 41: p. 849.
   D. W. Talmage, Allergy and Immunology. Ann. Rev. Med., 1957. 8: p. 239.
6. F. M. Burnet, A Modification of Jerne's Theory of Antibody Production Using the Concept of Clonal Selection. Aust. J. Sci., 1957. 20: p. 67.
7. D. R. Davies and S. Chacko, Antibody Structure. Accounts Chem. Res., 1993. 26: p. 421-427.
8. N. K. Jerne, The Generative Grammar of the Immune System, in Nobel Lectures, Physiology or Medicine 1981-1990, J. Lindsten, Editor. 1993, World Scientific Publishing Co.: Singapore. p. 211-225.
9. G. Köhler and C. Milstein, Continuous cultures of fused cells secreting antibody of predefined specificity. Nature, 1975. 256: p. 495-497.
10. G. J. F. Köhler, Derivation and Diversification of Monoclonal Antibodies, in Nobel Lectures, Physiology or Medicine 1981-1990, J. Lindsten, Editor. 1993, World Scientific Publishing Co.: Singapore. p. 228-243.
11. C. Milstein, From the Structure of Antibodies to the Diversification of the Immune Response, in Nobel Lectures, Physiology or Medicine 1981-1990, J. Lindsten, Editor. 1993, World Scientific Publishing Co.: Singapore. p. 248-270.
12. R. B. Merrifield, Solid Phase Peptide Synthesis. I. The Synthesis of a Tetrapeptide. J. Am. Chem. Soc., 1963. 85: p. 2149-2154.
13. R. B. Merrifield, Solid Phase Peptide Synthesis. II. The Synthesis of Bradykinin. J. Am. Chem. Soc., 1964. 86: p. 304.
14. R. B. Merrifield, Solid-Phase Peptide Synthesis, III. An Improved Synthesis of Bradykinin. Biochem., 1964. 3: p. 1385-1390.
15. B. Merrifield, Solid Phase Synthesis, in Nobel Lectures, Chemistry 1981-1990, T. Frängsmyr, Editor. 1992, World Scientific Publishing Co.: Singapore. p. 149-175.
16. K. Kirshenbaum, A. E. Barron, R. A. Goldsmith, P. Armand, E. K. Bradley, K. T. V. Truong, K. A. Dill, F. E. Cohen, and R. N. Zuckermann, Sequence-specific polypeptoids: A diverse family of heteropolymers with stable secondary structure. Proc. Natl. Acad. Sci. USA, 1998. 95: p. 4303-4308.
17. M. Egholm, E. Buchardt, P. E. Nielsen, and R. H. Berg, Peptide nucleic acids (PNA). Oligonucleotide analogues with an achiral peptide backbone. J. Am. Chem. Soc., 1992. 114: p. 1895-1897.
18. G. P. Dado and S. H. Gellman, Intramolecular Hydrogen Bonding in Derivatives of Beta-Alanine and Gamma-Amino Butyric Acid: Model Studies for the Folding of Unnatural Polypeptide Backbones. J. Am. Chem. Soc., 1994. 116: p. 1054-1062.
19. D. H. Appella, L. A. Christianson, I. L. Karle, D. R. Powell, and S. H. Gellman, Peptide Foldamers: Robust Helix Formation in a New Family of Beta-Amino Acid Oligomers. J. Am. Chem. Soc., 1996. 118: p. 13071-13072.
20. K. Yue and K. A. Dill, Inverse Protein Folding Problem: Designing Polymer Sequences. Proc. Natl. Acad. Sci. USA, 1992. 89: p. 4163-4167.
21. S. H. Gellman, Foldamers: A Manifesto. Accounts Chem. Res., 1998. 31: p. 173-180.
22. K. Kirshenbaum, R. N. Zuckermann, and K. A. Dill, Designing polymers that mimic biomolecules. Current Opinion in Structural Biology, 1999. 9: p. 530-535.
23. P. Koehl and M. Levitt, De Novo Protein Design. I. In Search of Stability and Specificity. J. Mol. Biol., 1999. 293: p. 1161-1181.
24. P. Koehl and M. Levitt, De Novo Protein Design. II. Plasticity in Sequence Space. J. Mol. Biol., 1999. 293: p. 1183-1193.
25. E. I. Shakhnovich and A. M. Gutin, Engineering of stable and fast-folding sequences of model proteins. Proc. Natl. Acad. Sci. USA, 1993. 90: p. 7195-7199.
26. V. S. Pande, A. Y. Grosberg, and T. Tanaka, Folding Thermodynamics and kinetics of imprinted renaturable heteropolymers. J. Chem. Phys., 1994. 101(9): p. 8246-8257.
27. V. S. Pande, A. Y. Grosberg, and T. Tanaka, Thermodynamic procedure to synthesize heteropolymers that can renature to recognize a given target molecule. Proc. Natl. Acad. Sci. USA, 1994. 91: p. 12976-12979.
28. V. S. Pande, A. Y. Grosberg, and T. Tanaka, Phase diagram of heteropolymers with an imprinted conformation. Macromolecules, 1995. 28: p. 2218-2227.
29. V. S. Pande, A. Y. Grosberg, and T. Tanaka, How to Create Polymers with Protein-Like Capabilities: A Theoretical Suggestion. Physica D, 1997. 107: p. 316-321.
30. K. Mosbach and O. Ramstrom, The Emerging Technique of Molecular Imprinting and its Future Impact on Biotechnology. Biotechnol., 1996. 14: p. 163-170.
31. P. A. G. Cormack and K. Mosbach, Molecular imprinting: recent developments and the road ahead. Reactive and Functional Polymers, 1999. 41: p. 115-124.
32. K. Mosbach, Toward the next generation of molecular imprinting with emphasis on the formation, by direct molding, of compounds with biological activity(biomimetics). Anal. Chim. Acta, 2001. 435: p. 3-8.
33. M. Komiyama, T. Takeuchi, T. Mukawa, and H. Asanuma, Molecular Imprinting From Fundamentals to Applications. 2003, Weinheim, Germany: Wiley-VCH.
34. G. Wulff, A. Sarhan, and K. Zabrocki, Enzyme-Analogue Built Polymers and Their Use for the Resolution of Racemates. Tetrahedron Letters, 1973. 44: p. 4329-4332.
35. C. Yu and K. Mosbach, Influence of mobile phase composition and cross-linking density on the enantiomeric recognition properties of configurationally biomimetic imprinted polymers. J. Chromatogr. A, 2000. 888: p. 63-72.
36. H. S. Andersson, J. G. Karlsson, S. A. Piletsky, A.-C. Koch-Schmidt, K. Mosbach, and I. A. Nicholls, Study of the nature of recognition in configurationally biomimetic imprinted polymers, II. Influence of monomer-template ratio and sample load on retention and selectivity. J. Chromatogr. A, 1999. 848: p. 39-49.
37. D. Kriz, C. B. Kriz, L. I. Anderson, and K. Mosbach, Thin-Layer Chromatography Based on the Molecular Imprinting Technique. Anal. Chem., 1994. 66: p. 2636-2639.
38. J. Cederfur, Y. Pei, M. Zihui, and M. Kempe, Synthesis and Screening of a Configurationally biomimetic imprinted Polymer Library Targeted for Penicillin G. J. Comb. Chem., 2003. 5: p. 67-72.
39. M. Kempe and K. Mosbach, Separation of amino acids, peptides and proteins on configurationally biomimetic imprinted stationary phases. J. Chromatogr. A, 1995. 691: p. 317-323.

40. K. Haupt, K. Noworytab, and W. Kutner, Imprinted polymer-based enantioselective acoustic sensor using a quartz crystal microbalance. Anal. Commun., 1999. 36.

41. C. Liang, H. Peng, A. Zhou, L. Nie, and S. Yao, Molecular imprinting polymer coated BAW bio-mimic sensor for direct determination of epinephrine. Anal. Chim. Acta, 2000. 415: p. 135-141.

42. J. Z. Hilt, M. E. Byrne, and N. A. Peppas. Novel Biomimetic Polymer Networks: Development and Application as Selective Recognition Elements for Biomolecules at the Micro-/Nanoscale. in AIChE Nanoscale Science and Engineering Topical Conference Proceedings. 2003. San Francisco, Calif.

43. D. K. Robinson and K. Mosbach, Molecular imprinting of a transition state analogue leads to a polymer exhibiting esterolytic activity. J. Chem. Soc. Chem. Commun., 1989. 14: p. 969 - 970.

44. B. Sellergren and K. J. Shea, Enantioselective ester hydrolysis catalyzed by imprinted polymers. Tetrahedron-Asymmetry, 1994. 5: p. 1403-1406.

45. R. N. Karmalkar, M. G. Kulkarni, and R. A. Mashelkar, Configurationally biomimetic imprinted Hydrogels Exhibit Chymotrypsin-like Activity. Macromolecules, 1996. 29: p. 1366-1368.

46. O. Ramström and K. Mosbach, Synthesis and catalysis by configurationally biomimetic imprinted materials. Curr. Opin. Chem. Biol., 1999. 3: p. 759-764.

47. L. Andersson, B. Sellergren, and K. Mosbach, Imprinting of Amino Acid Derivatives in Macroporous Polymers. Tetrahedron Letters, 1984. 25(45): p. 5211-5214.

48. G. Vlatakis, L. J. Andersson, R. Muller, and K. Mosbach, Drug assay using antibody mimics made by molecular imprinting. Nature, 1993. 361: p. 645-647.

49. R. A. Bartsch and M. Maeda, eds. Molecular and Ionic Recognition with Imprinted Polymers. ACS Symposium Series. 1998, ACS: Washington, D.C.

50. L. I. Andersson, Molecular Imprinting as an Aid to Drug Bioanalysis, in Drug Development Assay Approaches, Including Molecular Imprinting and Biomarkers, E. Reid, H. M. Hill, and I. D. Wilson, Editors. 1998, The Royal Society of Chemistry: Cambridge, UK.

51. G. Odian, Principles of Polymerization. 1991, New York: Wiley.

52. G. Wulff, J. Vietmeier, and H.-G. Poll, Enzyme-analogue built polymers, 22: Influence of the nature of the crosslinking agent on the performance of imprinted polymers in racemic resolution. Makromolekul. Chem., 1987. 188: p. 731-740.

53. B. D. Ratner, The Engineering of Biomaterials Exhibiting Recognition and Specificity. J. Mol. Recognition, 1996. 9: p. 617-625.

54. N. A. Peppas and R. Langer, Advances in Biomaterials, Drug Delivery, and Bionanotechnology. AIChE J., 2003. 49(12): p. 2990-3006.

55. M. E. Byrne, K. Park, and N. A. Peppas, Molecular imprinting within hydrogels. Adv. Drug Deliver. Rev., 2002. 54(1): p. 149-161.

56. M. E. Byrne, K. Park, and N. A. Peppas. Biomimetic Networks for Selective Recognition of Biomolecules. 2002: Materials Research Society.

57. J. Z. Hilt, A. K. Gupta, R. Bashir, and N. A. Peppas, Ultrasensitive Biomems Sensors Based on Microcantilevers Patterned with Environmentally Responsive Hydrogels. Biomedical Microdevices, 2003. 5(3): p. 177-184.

58. E. Oral and N. A. Peppas, Responsive and recognitive hydrogels using star polymers. J. Biomed. Mater. Res. A, 2004. 68: p. 439-447.

59. P. Parmpi and P. Kofinas, Biomimetic glucose recognition using configurationally biomimetic imprinted hydrogels. Biomaterials, 2004. 25: p. 1969-1973.

60. L. D. V. Bolisay, J. F. March, W. E. Bentley, and P. Kofinas, Separation of baculoviruses using configurationally biomimetic imprinted polymer hydrogels. Mat. Res. Soc. Symp. Proc., 2004. 787: p. G3.1/1-G3.1/5.

61. D. R. Shnek, D. W. Pack, D. Y. Sasaki, and F. H. Arnold, Specific Protein Attachment to Artificial Membranes via Coordination to Lipid-Bound Copper(11). Langmuir, 1994. 10: p. 2382-2388.

62. M. Kempe, M. Glad, and K. Mosbach, An approach towards surface imprinting using the enzyme ribonuclease A. J. Mol. Recognition, 1995. 8(1-2): p. 35-39.

63. L. I. Andersson, R. Muller, G. Vlatakis, and K. Mosbach, Mimics of the Binding Sites of Opiod Receptors Obtained by Molecular Imprinting of Enkephalin and Morphine. Proc. Natl. Acad. Sci. USA, 1995. 92: p. 4788-4792.

64. D. L. Venton and E. Gudipati, Influence of protein on polysiloxane polymer formation: evidence for induction of complementary protein-polymer interactions. Biochim. Biophys. Acta, 1995. 1250: p. 126-136.

65. A. Rachkov and N. Minoura, Towards Configurationally biomimetic imprinted Polymers Selective to Peptides and Proteins. The Epitope Approach. Biochimica et Biophysica Acta, 2001. 1544: p. 255-266.

66. L. J. Harris, S. B. Larson, K. W. Hasel, and A. McPherson, Refined Structure of an Intact IgG2a Monoclonal Antibody. Biochem., 1997. 36: p. 1581-1597.

67. H. M. Berman, J. Westbrook, Z. Feng, G. Gilliland, T. N. Bhat, H. Weissig, I. N. Shindyalov, and P. E. Bourne, The Protein Data Bank. Nucleic Acids Res., 2000. 28: p. 235-242.

68. D. R. Burton, Monoclonal Antibodies from Combinatorial Libraries. Accounts Chem. Res., 1993. 26: p. 405-411.

69. J. Tormo, D. Blaas, N. R. Parry, D. Rowlands, D. Stuart, and I. Fita, Crystal Structure of a Human Rhinovirus Neutralizing Antibody Complexed with a Peptide Derived from Viral Capsid Protein VP2. EMBO J., 1994. 13: p. 2247-2256.

70. L. Stryer, Biochemistry. 4th ed. 1995, New York: W. H. Freeman.

71. K. Mosbach, K. Haupt, X.-C. Liu, P. A. G. Cormack, and O. Ramstrom, Molecular Imprinting: Status Artis et Quo Vadere, in Molecular and Ionic Recogniton with Imprinted Polymers, R. A. Bartsch and M. Maeda, Editors. 1998, American Chemical Society: Washington, D.C.

Additional References

Burt S. Essential Oils: their antibacterial properties and potential applications in food—a review. International Journal of Food Microbiology 94 (2004) pp. 223-253

Canal, T.; Peppas, N. A. J. Biomed. Mater. Res. (1989) 23, 1183.

Chang C. P., Dobashi T. Preparation of alginate complex capsules containing eucalyptus essential oil and its controlled release. Colloids and Surfaces B: Biointerfaces 32 (2003) pp.257-262

Duclairoir C., Orecchioni A. M., Depraetere P., Osterstock F., Nakache E. Evaluation of gliadins nanoparticles as drug delivery systems: a study of three different drugs. International Journal of Pharmaceutics, 253 (2003) p. 133-144

Franzios G., Mirotsou M., Hatziapostolou E., Kral J., Scouras Z. G., Mavragani-Tsipidou P. Insecticidal and genotoxic activities of mint essential oils. Journal of Agricultural and Food Chemistry, 45 (1997) pp. 2690-2694

Hartmans K. J., Diepenhorst P. The use of carvone as a sprout inhibitor for potatoes. Potato Research, 37 (1994) pp. 445-446

Hartmans K. J., Lenssen J. M., De Vries R. G. Use of talent (carvone) as a sprout growth regulator of seed potatoes and the effect on stm and tuber number, Potato Research, 41 (1998) pp. 190-191

Muller N. J. United States Patent Application 20020071877 (2002)

Peppas N. A., Am Ende D. J. Controlled release of perfumes from polymers. II. Incorporation and release of essential oils from glassy polymers, Journal of Applied Polymer Science, Vol. 66 (1997) pp. 509-513

Peppas N. A., Brannon-Peppas L. Controlled Release of fragrance from polymers I. Thermodynamic analysis. Journal of Controlled Release 40 (1996) 245-250

Sanchez I. C. Equilibrium distribution of a minor constituent between a polymer and its environment, in Durability of Macromolecular Materials, R. K. Eby, ed. ACS Symp. Ser. Vol. 95, American Chemical Society, Washington, DC, 1979, pp. 171-181

Sanchez I. C., Chang S. S. and Smith L. E. Migration models for polymer additives, Polym. News 6 (1980) 249-256

Secouard S., Malhiac C., Grisel M., Decroix B. Release of limonene from polysaccharide matrices: viscosity and synergy effect. Food Chemistry 82 (2003) 227-234

What is claimed is:

1. A composition comprising:
   a molecule-imprinted polymeric network comprising
   a polymer comprising acrylamide and ethylene glycol dimethacrylate imprinted with glucose molecule,
   one or more pores in the polymer wherein the one or more pores are micropores or nanopores that recognize a glucose molecule;
   one or more active agents in contact with the one or more pores and the polymer to form an active agent-load, molecule-imprinted polymeric network, wherein the one or more active agents comprise insulin, wherein subsequent contact with the glucose molecule creates internal stresses that rupture the polymeric network at the one or more pores,
   wherein the molecule-imprinted polymeric network is encapsulated with at least one coating layer containing an active agent layer;
   wherein rupture of the active agent-load, molecule-imprinted polymeric network is by at least one of:
   osmosis upon recognition and binding of the glucose molecule leading to rupture due to swelling;
   change of the solubility of the active agent-load, molecule-imprinted polymeric network leading to polymer dissolution; or
   local temperature changes leading to expansion of the active agent-load, molecule-imprinted polymeric network and combinations thereof.

2. The composition of claim 1, wherein the composition is encapsulated and comprises a surfactant, a bleaching agent, a corrosion inhibitor, a sudsing modifier, a fluorescent whitening agent, one or more enzymes, an anti redeposition agent, a color, one or more additives and combinations thereof.

3. The composition of claim 1, wherein the one or more active agents are released upon a change in solubility, pressure, a pH shift, a change in temperature, a temperature increase, enzymatic breakdown, diffusion and combinations thereof.

4. The composition of claim 1, wherein the molecule-imprinted polymeric network is formed into one or more layers to form a multilayer active agent-load, molecule-imprinted polymeric network.

5. The composition of claim 1, further comprising a second coating layer covering the active agent-load, molecule-imprinted polymeric network, wherein the second coating layer comprises a second polymer comprising one or more second pores in the second polymer that recognize a second molecule and subsequent contact with the second molecule creates internal stresses that rupture the second coating layer which provides a barrier to the release of one or more different active, one or more inert agents or both.

6. The composition of claim 1, wherein the molecule-imprinted polymeric network is formed into a sphere, film, planar, semi-spherical, cylinder, rod, hemispheres, conical, hemi-cylinders and combination thereof.

7. The composition of claim 1, wherein the molecule-imprinted polymeric network is at least partially porous.

8. An active agent-loaded, molecule-imprinted polymeric recognitive network composition comprising:
   a molecule-imprinted polymeric network disposed about a polymer core comprising
   one or more molecule imprinted coating layers independently comprising an acrylamide and ethylene glycol dimethacrylate polymer imprinted with one or more glucose molecules,
   one or more pores in the acrylamide and ethylene glycol dimethacrylate polymer that recognize a glucose molecule wherein the one or more pores are micropores or nanopores;
   one or more active agents in contact with the one or more pores to form an active agent-load, molecule-imprinted polymeric network, wherein the one or more active agents comprise insulin, wherein subsequent contact with the glucose molecule creates internal stresses that rupture the polymeric network at the one or more pores,
   wherein the one or more molecule imprinted coating layers is encapsulated with at least one coating layer containing an active agent layer;
   wherein rupture of the active agent-load, molecule-imprinted polymeric network is by at least one of:
   osmosis upon recognition and binding of the glucose molecule leading to rupture due to swelling;
   change of the solubility of the active agent-load, molecule-imprinted polymeric network leading to polymer dissolution; or
   local temperature changes leading to expansion of the active agent-load, molecule-imprinted polymeric network and combinations thereof.

* * * * *